(12) United States Patent
Hu et al.

(10) Patent No.: US 12,324,832 B2
(45) Date of Patent: Jun. 10, 2025

(54) **APPLICATION OF HEPTOGLYCAN-CHAIN-CONTAINING OLIGOSACCHARIDE COMPOUNDS IN PREPARATION OF VACCINE AGAINST *HELICOBACTER PYLORI***

(71) Applicants: Jing Hu, Wuxi (CN); Jian Yin, Wuxi (CN)

(72) Inventors: Jing Hu, Wuxi (CN); Jian Yin, Wuxi (CN)

(73) Assignee: Jiangnan University, Wuxi (CN)

( * ) Notice: Subject to any disclaimer, the term of this patent is extended or adjusted under 35 U.S.C. 154(b) by 919 days.

(21) Appl. No.: 17/391,061

(22) Filed: Aug. 2, 2021

(65) Prior Publication Data

US 2021/0369834 A1    Dec. 2, 2021

Related U.S. Application Data

(63) Continuation of application No. PCT/CN2020/097646, filed on Jun. 23, 2020.

(30) Foreign Application Priority Data

Apr. 13, 2020 (CN) .......................... 202010285718.5

(51) Int. Cl.
  *A61K 39/02* (2006.01)
  *C07H 1/00* (2006.01)
  *C07H 3/06* (2006.01)

(52) U.S. Cl.
  CPC ............. *A61K 39/105* (2013.01); *C07H 1/00* (2013.01); *C07H 3/06* (2013.01)

(58) Field of Classification Search
  CPC ........... A61K 39/105; C07H 1/00; C07H 3/06
  See application file for complete search history.

(56) References Cited

U.S. PATENT DOCUMENTS 11,566,040 B2 *   1/2023   Yin .......................... A61P 31/04
12,018,306 B2 *   6/2024   Yin .......................... C12P 19/04

FOREIGN PATENT DOCUMENTS

CN          109776632 A  *  5/2019  ............... A61P 1/04

OTHER PUBLICATIONS

CN109776632A, Machine English translation done on Sep. 9, 2024.*
Tian G. et al. Chemical Synthesis and Immunological Evaluation of Helicobacter pylori Serotype O6 Tridecasacchride O-Antigen containing a DD Heptoglycan. Angew. Chem. Int. Ed. 2020, 32(59):13362-13370.
Altam E, et al. Occurrence of a nontypable Helicobacter pylori strain lacking Lewis blood group O-antigens and DD-heptoglycan: evidence for the role of the core a1,6-glucan chain in colonization. Glycobiology. 2003 vol. 13 No. 11 pp. 777-783.

* cited by examiner

*Primary Examiner* — Pancham Bakshi
(74) *Attorney, Agent, or Firm* — Lili Chen

(57) ABSTRACT

Disclosed is the application of heptoglycan-chain-containing oligosaccharide compounds in preparation of a vaccine against *Helicobacter pylori*, belonging to the field of medicine. Different antigen oligosaccharides were obtained by chemical synthesis and fixed onto a chip surface to prepare a synthetic oligosaccharide chip. With animal immunization experiments and synthetic oligosaccharide chip analysis, the antibodies in antiserum produced by *Helicobacter pylori* polysaccharide immunization are used to determine the structure-activity relationship between the synthetic oligosaccharides and immunogenicity. It is found that the heptoglycan chain in the oligosaccharide compounds is an important immune epitope, and oligosaccharides containing α-(1→3) heptoglycan chain can be used in preparation and development of vaccines for prevention and treatment of *Helicobacter pylori* infection.

4 Claims, 7 Drawing Sheets

APPLICATION OF HEPTOGLYCAN-CHAIN-CONTAINING OLIGOSACCHARIDE COMPOUNDS IN PREPARATION OF VACCINE AGAINST *HELICOBACTER PYLORI*

CROSS-REFERENCE TO RELATED APPLICATIONS

This application is a continuation of international application PCT/CN2020/097646, filed Jun. 23, 2020, which claims the benefit of priority to Chinese patent application No. CN2020102857185, filed Apr. 13, 2020, the content of which are hereby incorporated by reference in the entirety.

BACKGROUND OF THE INVENTION

Field of the Invention

The present invention relates to the field of medicine, and in particular to the application of heptoglycan-chain-containing oligosaccharide compounds in preparation of a vaccine against *Helicobacter pylori*.

Description of the Related Art

*Helicobacter pylori* is a microaerophilic gram-negative pathogen. As one of the most widespread bacterial pathogens, *Helicobacter pylori* has an infection rate of about 50% in the world population (J. G. Kusters et al., *Clin Microbiol Rev*, 2006, 19: 449). Researches have shown that *Helicobacter pylori* is the main cause of diseases such as gastritis, gastric atrophy, peptic and duodenal ulcers and the like (B. Molnar et al., *Dig Dis*, 2010, 28: 604). In addition, since *Helicobacter pylori* infection is directly related to the increased risk of gastric cancer (L. E. Wroblewski et al., *Clin Microbiol Rev*, 2010, 23: 713; C. Prinz et al., *World J Gastroenterol*, 2006, 12: 5458), in 1994, the World Health Organization (WHO) classified it as a Category I human carcinogen (*Lyon: IARC*, 1994, 61: 177). Researches have shown that *Helicobacter pylori* infection increases the risk of gastric cancer by 2-8 times (*Helicobacter* and Cancer Collaborative Group, *Gut*, 2001, 49: 347; F. Kamangar et al., *J Natl Cancer Inst*, 2006, 98: 1445).

At present, *Helicobacter pylori* infection is treated mainly by a triple or quadruple therapy using bismuth or proton pump inhibitors combined with antibiotics. However, antibiotic-based treatment (mainly clarithromycin) has many disadvantages. Long-term use of antibiotics may lead to the emergence of bacterial resistance (G. Ayala et al., World J gastroenterol, 2014, 20: 1450; N. Vakil, Cancer J Gastroenterol, 2003, 17: 30B), and the antibiotics-based treatment cannot prevent the risk of *Helicobacter pylori* reinfection. There is an urgent need to develop new therapies for treatment of *Helicobacter pylori*. A *Helicobacter pylori* vaccine is considered to be the most effective method to control this global infectious disease (M. Selgrad et al., *Curr Opin Pharrnacol*, 2008, 8: 593). Although researchers have made many efforts in the development of vaccines against *Helicobacter pylori*, for example, in 2009, a fusion protein vaccine including urease B subunit and heat-labile enterotoxin B subunit was licensed in China (M. Zeng et al., *Lancet*, 2015, 386: 1457), no vaccine against *Helicobacter pylori* infection has yet been successfully marketed. Lipopolysaccharide (LPS) O-antigen, as the main component of the *Helicobacter pylori* cell surface, is considered to be an attractive vaccine candidate (S. Yu et al., *Infection and Immunity*, 2007, 75: 2974; D. Ren et al., *Vaccine*, 2011, 29: 4210). Researches have shown that the development of carbohydrate-based vaccines against *Helicobacter pylori* infection is very promising, and carbohydrate-based conjugate vaccines have been successfully used to prevent systemic infection and inhibit host colonization (J. H. Passwell et al., *Infection and Immunity*, 2001, 69: 1351). However, the structure of the extracted lipopolysaccharide is not specific, it is easy to have the characteristics of similar impurities in the structure and the experiment repeatability is poor, which limits the application of the extracted lipopolysaccharide as vaccine treatment. Therefore, there is an urgent need to develop a vaccine that has a specific structure, can be chemically synthesized and has an excellent inhibitory effect on *Helicobacter pylori*.

SUMMARY OF THE INVENTION

The present invention provides a solution to aforementioned problems (e.g., structural diversity and poor reproducibility) of using extracted carbohydrates in preparation of *Helicobacter pylori* vaccines. Different carbohydrate antigen oligosaccharides are obtained by chemical synthesis. Synthetic oligosaccharide antigens are fixed onto a chip through an amino linker to prepare an oligosaccharide chip. Polysaccharide antiserum is obtained through animal immunization with *Helicobacter pylori* lipopolysaccharide extract. The antibody composition and titer are analyzed using the synthetic oligosaccharide chip, the immunological epitope is analyzed at the molecular level, and the structure-activity relationship between oligosaccharide chains and immunocompetence is investigated. The invention provides synthetic carbohydrate antigens for preparation and development of vaccines for prevention and treatment of *Helicobacter pylori* infection.

A first objective of the invention is to provide an application of heptoglycan-chain-containing oligosaccharide compounds of Formula (I) in preparation of a vaccine against *Helicobacter pylori*,

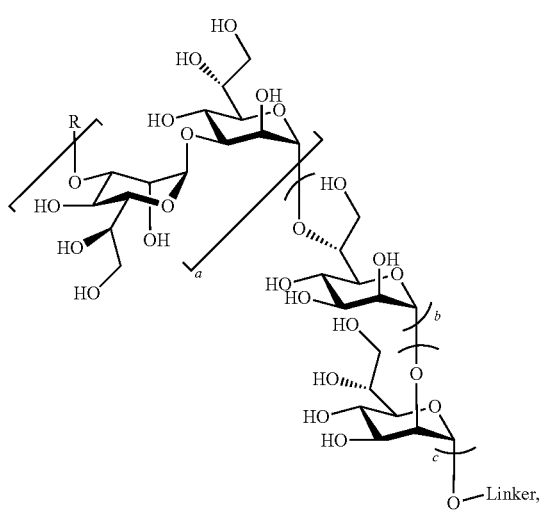

I wherein R is H or

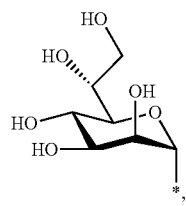

wherein * is the linking site; a=1-100; b=0-100; c=0-100; the linker includes an amino linker —(CH$_2$)$_n$—NH$_2$; and n represents the number of (CH$_2$) in the amino linker, wherein n=2-40.

In an embodiment of the invention, "a" in Formula I may not be 0; and "b" and "c" in Formula I may be 0 at the same time.

In an embodiment of the invention, a in Formula I is further preferably 1-5.

In an embodiment of the invention, b in Formula I is further preferably 0-2.

In an embodiment of the invention, c in Formula I is further preferably 0-2.

In an embodiment of the invention, n in the amino linker is further preferably 2-10.

In an embodiment of the invention, the heptoglycan-chain-containing oligosaccharide compounds include an α-(1→3)-heptoglycan chain, and do not contain a Lewis antigen fragment.

The Lewis antigen fragment is defined as fucosylated oligosaccharides observed in endodermal epithelia and red blood cells. These structures have been shown to be expressed in normal tissues on two major oligosaccharide chains, Lewis$^{a/b}$ and Lewis$^{x/y}$, according to the linkage type between the Gal residue and the GlcNAc residue, β1,3 and β1,4, respectively.

In an embodiment of the invention, the heptoglycan-chain-containing oligosaccharide specifically includes a compound of the following structures:

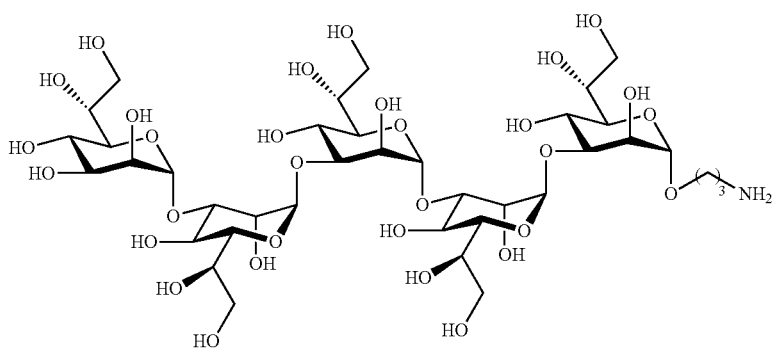

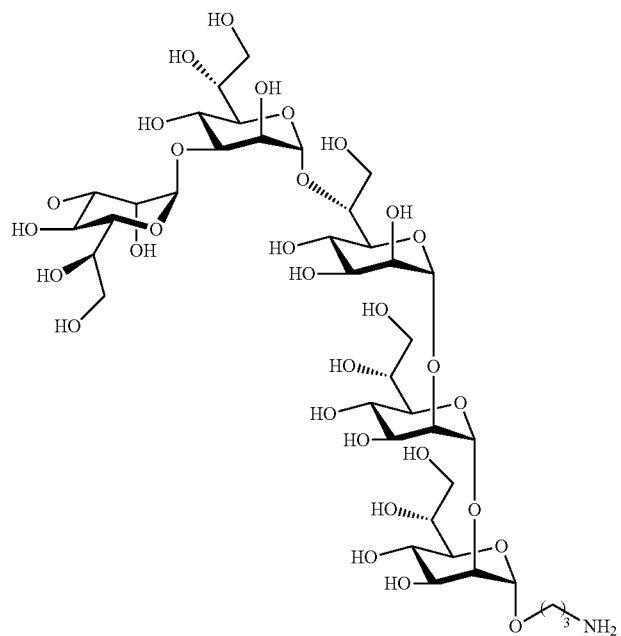
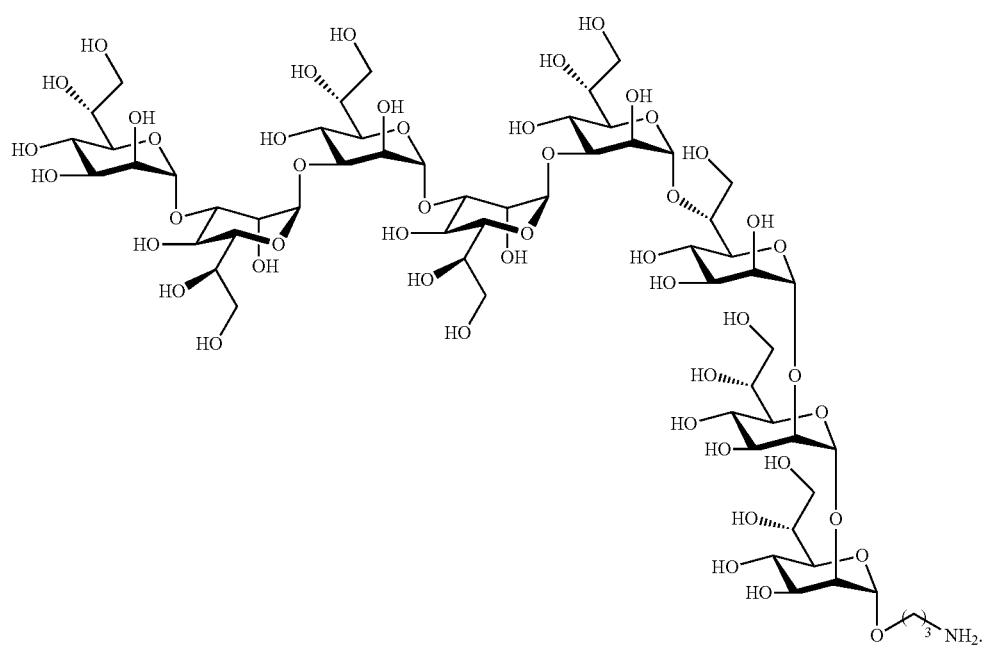

In an embodiment of the invention, a preparation method of the heptoglycan-chain-containing oligosaccharide compounds includes the following steps:
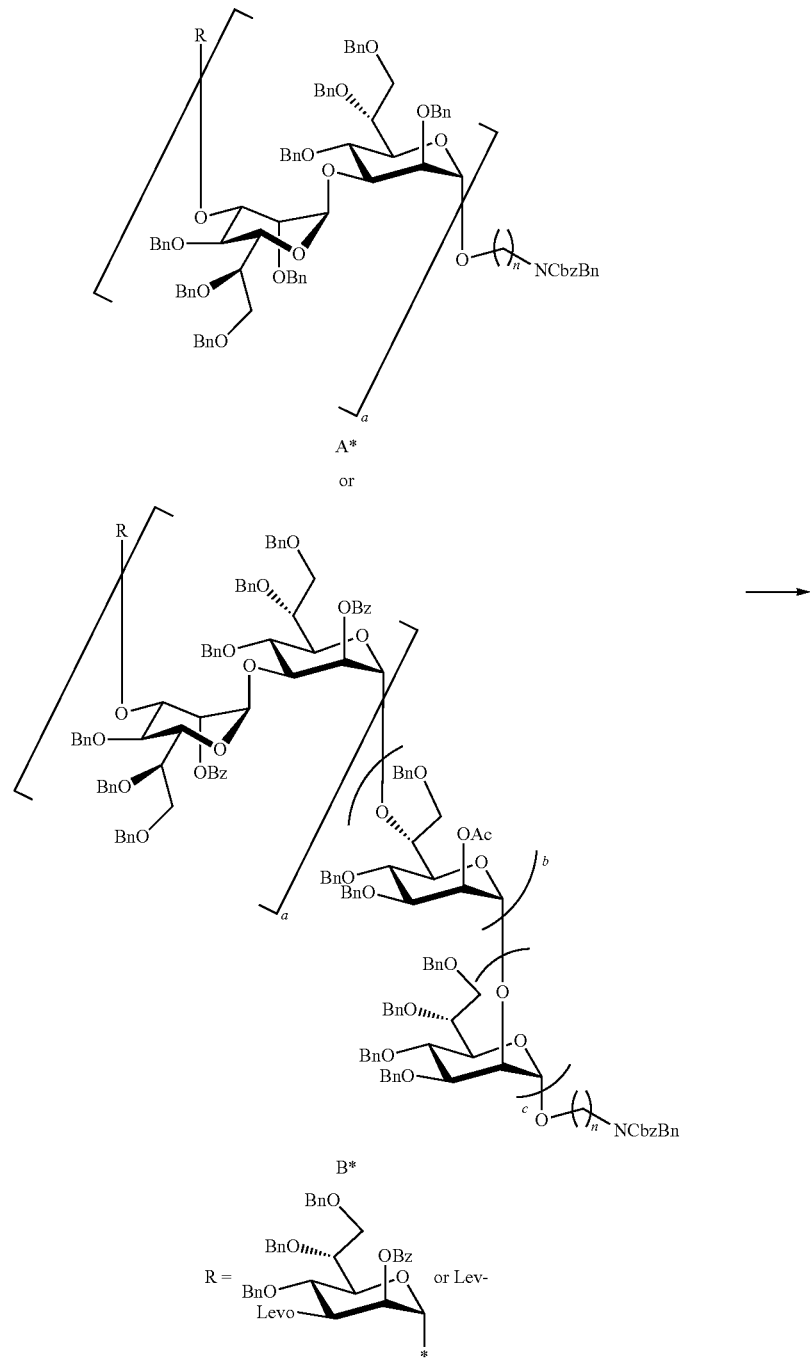

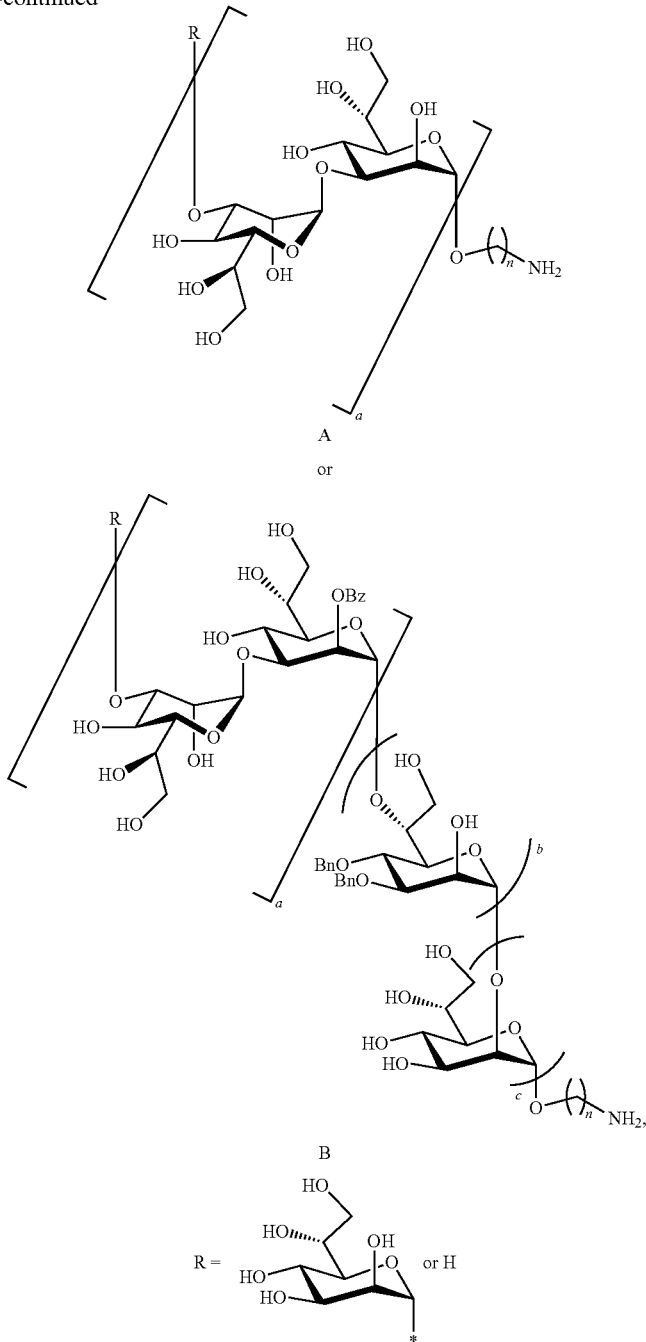

(1) dissolving compound A* or compound B* in an organic solvent, adding an alkaline reagent for deprotection, and obtaining an intermediate compound after the completion of the deprotection reaction; and (2) dissolving the intermediate compound obtained in step (1) in a solvent, adding a Pd/C reducing agent, and carrying out a reduction reaction under hydrogen conditions to obtain the target compound A or B.

In an embodiment of the invention, the organic solvent in step (1) is any one or a mixture of tetrahydrofuran (THF) and methanol (MeOH).

In an embodiment of the invention, the organic solvent in step (1) is preferably a mixed system of tetrahydrofuran and methanol. A volume ratio of THF:MeOH is 1:1.

In an embodiment of the invention, the alkali reagent in step (1) is an organic base and/or an inorganic base. The organic base includes sodium methoxide, and the inorganic base includes any one or more of sodium hydroxide, potassium hydroxide, sodium carbonate and potassium carbonate.

In an embodiment of the invention, step (1) specifically includes the following process:

dissolving compound A* or compound B* in THF/MeOH (1:1, v/v, 2.0 mL), adding CH$_3$ONa, stirring the mixture at room temperature for 0.5 hr, then adding NaOH (aq, 1 M, 200 µL), and stirring the reaction mixture at room temperature for 12 hr.

In an embodiment of the invention, step (1) includes: after the completion of the reaction, adding Amerlite IR 120 (H⁺) resin to neutralize the pH of the reaction solution to less than 7, filtering the solution, concentrating the filtrate, and carrying out separation and purification by silica gel column chromatography.

In an embodiment of the invention, the solvent in step (2) is a mixed system composed of MeOH, THF, $H_2O$ and AcOH. A volume ratio of MeOH:THF:$H_2O$:AcOH is 10:5:4:1.

The invention relates to extraction and purification of *Helicobacter pylori* serotype O6 LPS to immunize New Zealand rabbits to obtain antiserum, and analysis of antibody binding activity of chemically synthesized *Helicobacter pylori* serotype O6 oligosaccharide fragments.

The invention chemically synthesizes heptose chain-containing oligosaccharide compounds of different *Helicobacter pylori* serotype O6 oligosaccharide fragments for the first time, and the antigenic activity of chemically synthesized *Helicobacter pylori* serotype O6 oligosaccharide fragments are assessed by antibody binding assays.

In an embodiment of the invention, it provides an oligosaccharide chip. The oligosaccharide chip is prepared by fixing the heptoglycan-chain-containing oligosaccharide compounds of Formula (I) onto a chip surface though its amino linker.

In an embodiment of the invention, the synthetic oligosaccharides fixed on the chip surface were bound to antibodies in the antiserum, which is used to determine the structure-activity relationship between the synthetic oligosaccharides and the antigenic activity. The results show that the heptoglycan chain in the O-antigen is an important antigenic epitope. For example, heptoglycan-chain-containing pentasaccharide compound 3, pentasaccharide compound 4 and octasaccharide compound 6 may be well recognized by antibodies in the antiserum. On the other hand, the Lewis antigen may block the antibody binding activity. For example, Lewis-antigen-containing tridecasaccharide compound 7 was not recognized by the antibodies. The heptoglycan-chain-containing oligosaccharides of the invention may be used as a carbohydrate antigen in preparation and development of a vaccine for prevention and treatment of *Helicobacter pylori*.

In an embodiment of the invention, it further provides a vaccine for prevention and treatment of *Helicobacter pylori*, comprising the heptoglycan-chain-containing oligosaccharide compounds of Formula (I) as carbohydrate antigens.

In summary, a disaccharide, a trisaccharide, a pentasaccharide, an octasaccharide and a tridecasaccharide compound are respectively obtained by chemical synthesis methods. Reducing ends of the synthesized oligosaccharides are assembled with an amino linker, and the synthetic oligosaccharides are fixed onto a chip surface to prepare a synthetic oligosaccharide chip. In combination with animal immunization experiments and synthetic oligosaccharide chip analysis, the structure-activity relationship between the synthetic oligosaccharides and immunogenicity is determined. The results show that the heptoglycan chain in the antigen is an important antigenic epitope. Heptoglycan-chain-containing pentasaccharide 3, pentasaccharide 4 and octasaccharide 6 may be recognized by the rabbit serum antibody, but the Lewis-antigen-containing tridecasaccharide 7 was not be recognized by the antibody. The heptoglycan-chain-containing oligosaccharides of the invention may be used as a carbohydrate antigen in preparation and development of a vaccine for prevention and treatment of *Helicobacter pylori*.

DETAILED DESCRIPTION

Implementations of the invention will be described in detail below with reference to the examples. However, those skilled in the art will understand that the following examples are merely illustrative of the invention and should not be construed as limiting the scope of the invention. The examples in which specific conditions are not specified are carried out according to standard conditions known to the those skilled in the art or conditions recommended by the manufacturer. Those reagents or instruments whose manufacturers are not given are conventional products that are commercially available.

Example 1. Chemical Synthesis of Antigenic Oligosaccharide Compounds

Figure 1:
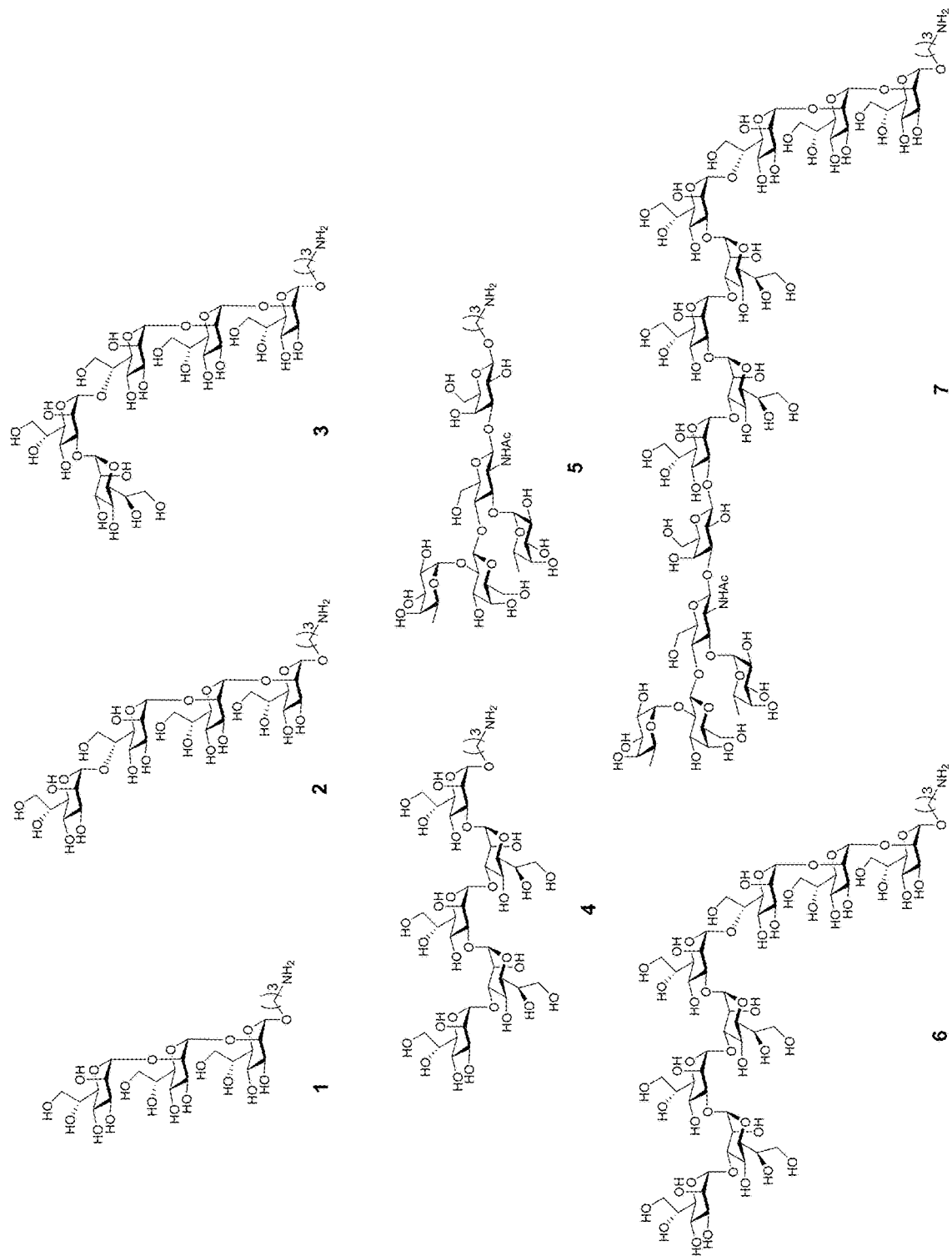
FIG. 1: Structural formulae of different antigen oligosaccharides.

Antigen oligosaccharide compounds are shown in FIG. 1.

For the synthesis of compounds 1, 2, 3, 4, 5, 6 and 7, using corresponding fully protected compounds 1*, 2*, 3*, 4*, 5*, 6* and 7* as starting materials (these compounds can be prepared with reference to patents CN201910156533.1 and CN109776632A), all acyl groups were removed under alkaline conditions. After purification, all benzyl and benzyloxycarbonyl groups were removed using 10% Pd/C and hydrogen to obtain fully deprotected target molecules 1, 2, 3, 4, 5, 6 and 7.

The experimental procedure is as follows:
Compound 1:

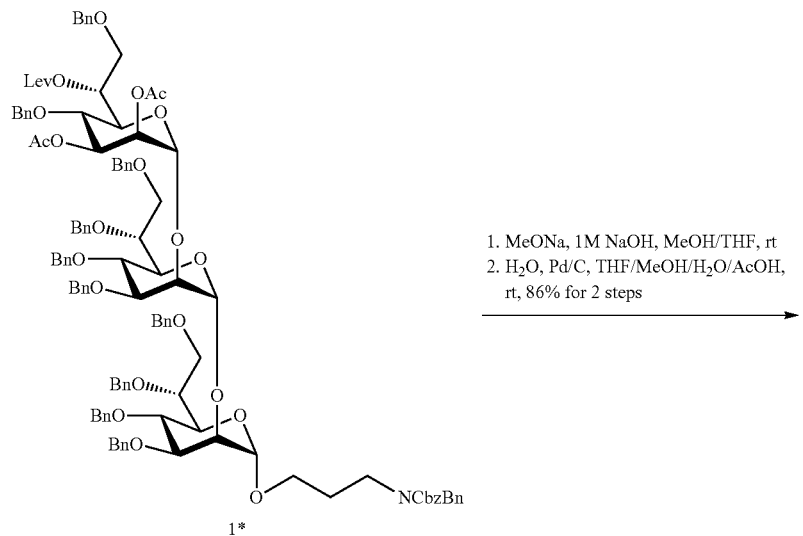

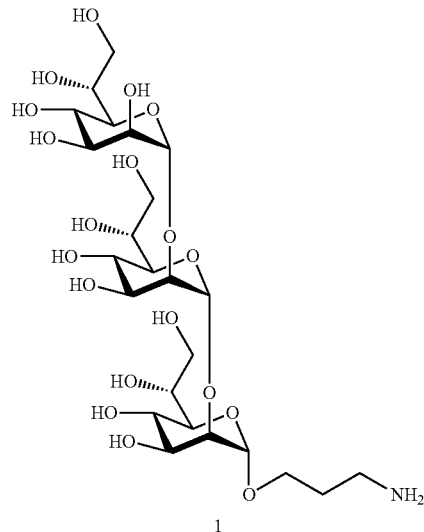

Compound 1* (28 mg, 0.0143 mmol) was dissolved in THF/MeOH (1:1, v/v, 2.0 mL), CH$_3$ONa (20 mg) was added, and the mixture was stirred at room temperature for 0.5 hr, followed by the addition of NaOH (aq, 1 M, 100 μL). The reaction mixture was stirred at room temperature for 12 hr. After the completion of the reaction was detected by TLC, Amerlite IR 120 (H$^+$) resin was added to neutralize the pH of the reaction solution to less than 7, the solution was filtered, and the filtrate was concentrated under reduced pressure, and was separated and purified by silica gel column chromatography (dichloromethane/methanol: 50/1) to obtain a product intermediate. The above deacylated compound was dissolved in MeOH/THF/H$_2$O/AcOH (10:5:4:1, v/v/v/v, 2 mL), 10% Pd/C (50 mg) was added, and the reaction mixture was stirred under hydrogen (1 bar) conditions for 48 hr. After the completion of the reaction was detected by time-of-flight mass spectrometry, the solution was filtered, the filtrate was concentrated and vacuum-dried, and the crude product was separated and purified by a Sephadex LH-20 gel column to obtain compound 1 (8 mg, 86% for two steps). $^1$H NMR (700 MHz, Deuterium Oxide) δ 5.22 (d, J=2.0 Hz, 1H, 1-H), 5.05 (d, J=1.9 Hz, 1H, 1-H), 4.93 (d, J=1.8 Hz, 1H, 1-H), 4.00-3.93 (m, 5H), 3.85 (dd, J=3.3, 1.8 Hz, 1H), 3.82-3.74 (m, 5H), 3.73 (dd, J=5.6, 3.0 Hz, 1H), 3.72-3.66 (m, 5H), 3.66-3.62 (m, 3H), 3.59 (dd, J=10.0, 2.9 Hz, 1H), 3.57-3.49 (m, 2H), 3.12-3.00 (m, 2H, CH$_2$), 1.92 (dddd, J=15.0, 12.0, 6.1, 3.8 Hz, 2H, CH$_2$). $^{13}$C NMR (176 MHz, Deuterium Oxide) δ 102.3, 100.5, 98.0, 78.8, 78.6, 74.0, 73.6, 73.3, 71.8, 71.5, 71.4, 70.7, 70.3, 70.1, 69.8, 67.5, 67.4, 67.2, 65.0, 61.7, 61.7, 61.6, 61.5, 37.5, 26.6. HRMS (ESI) m/z calcd for C$_{24}$H$_{46}$O$_{19}$N [M+H]$^+$ 652.2659, found 652.2700.

Compound 2:

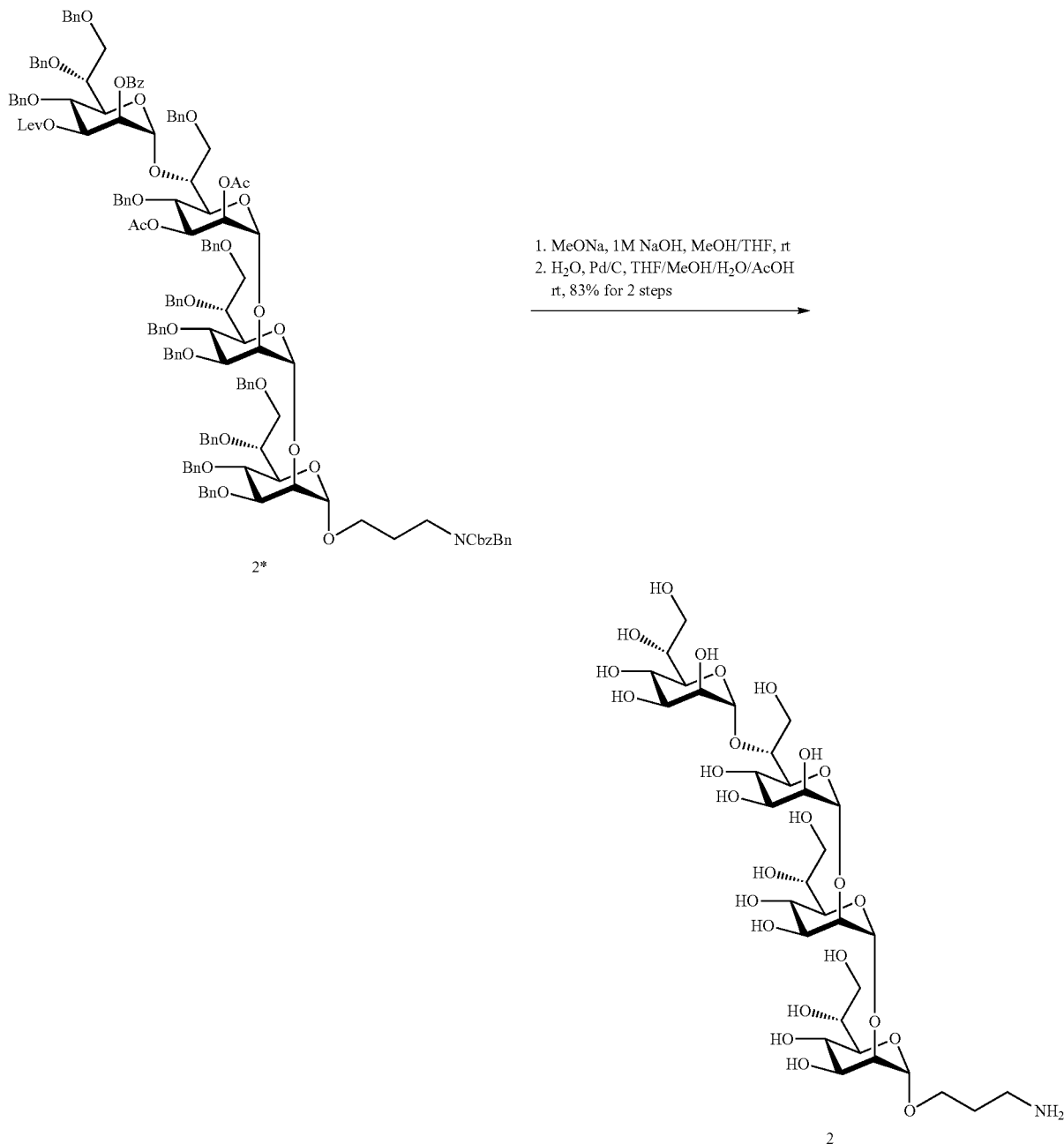

Compound 2* (30 mg, 0.0119 mmol) was dissolved in THF/MeOH (1:1, v/v, 3.0 mL), CH₃ONa (20 mg) was added, and the mixture was stirred at room temperature for 0.5 hr, followed by the addition of NaOH (aq, 1 M, 200 μL). The reaction mixture was stirred at room temperature for 12 hr. After the completion of the reaction was detected by TLC, Amerlite IR 120 (H⁺) resin was added to neutralize the pH of the reaction solution to less than 7, the solution was filtered, and the filtrate was concentrated under reduced pressure, and was separated and purified by silica gel column chromatography (dichloromethane/methanol: 50/1) to obtain a half-deprotected product intermediate. The above deacylated compound was dissolved in MeOH/THF/H₂O/ AcOH (10:5:4:1, v/v/v/v, 3 mL), 10% Pd/C (60 mg) was added, and the reaction mixture was stirred under hydrogen (1 bar) conditions for 48 hr. After the completion of the reaction was detected by time-of-flight mass spectrometry, the solution was filtered, the filtrate was concentrated and vacuum-dried, and the crude product was separated and purified by a Sephadex LH-20 gel column to obtain compound 2 (8.3 mg, 83% for two steps). ¹H NMR (700 MHz, Deuterium Oxide) δ 5.17 (d, J=1.7 Hz, 1H, 1-H), 5.04 (d, J=1.9 Hz, 1H, 1-H), 4.99 (d, J=1.7 Hz, 1H, 1-H), 4.92 (d, J=1.9 Hz, 1H, 1-H), 4.06-3.99 (m, 2H), 3.99-3.90 (m, 5H), 3.88-3.82 (m, 2H), 3.83-3.74 (m, 7H), 3.74-3.69 (m, 4H), 3.69-3.65 (m, 3H), 3.65-3.60 (m, 1H), 3.58 (dd, J=10.1, 2.9

Hz, 1H), 3.06 (dddd, J=20.3, 15.1, 12.8, 7.8 Hz, 2H, CH$_2$), 1.92 (dq, J=14.1, 7.4, 7.0 Hz, 2H, CH$_2$). $^{13}$C NMR (176 MHz, Deuterium Oxide) δ 102.7, 100.6, 98.2, 98.0, 79.8, 78.6, 76.4, 74.0, 73.3, 72.7, 72.3, 72.1, 71.5, 71.1, 70.6, 70.6, 70.4, 70.3, 70.0, 69.7, 67.6, 67.5, 67.4, 66.7, 64.9, 62.1, 61.7, 61.4, 60.8, 37.5, 26.7. HRMS (ESI) m/z calcd for C$_{31}$H$_{58}$O$_{25}$N [M+H]$^+$ 844.3292, found 844.3335.

Compound 3:

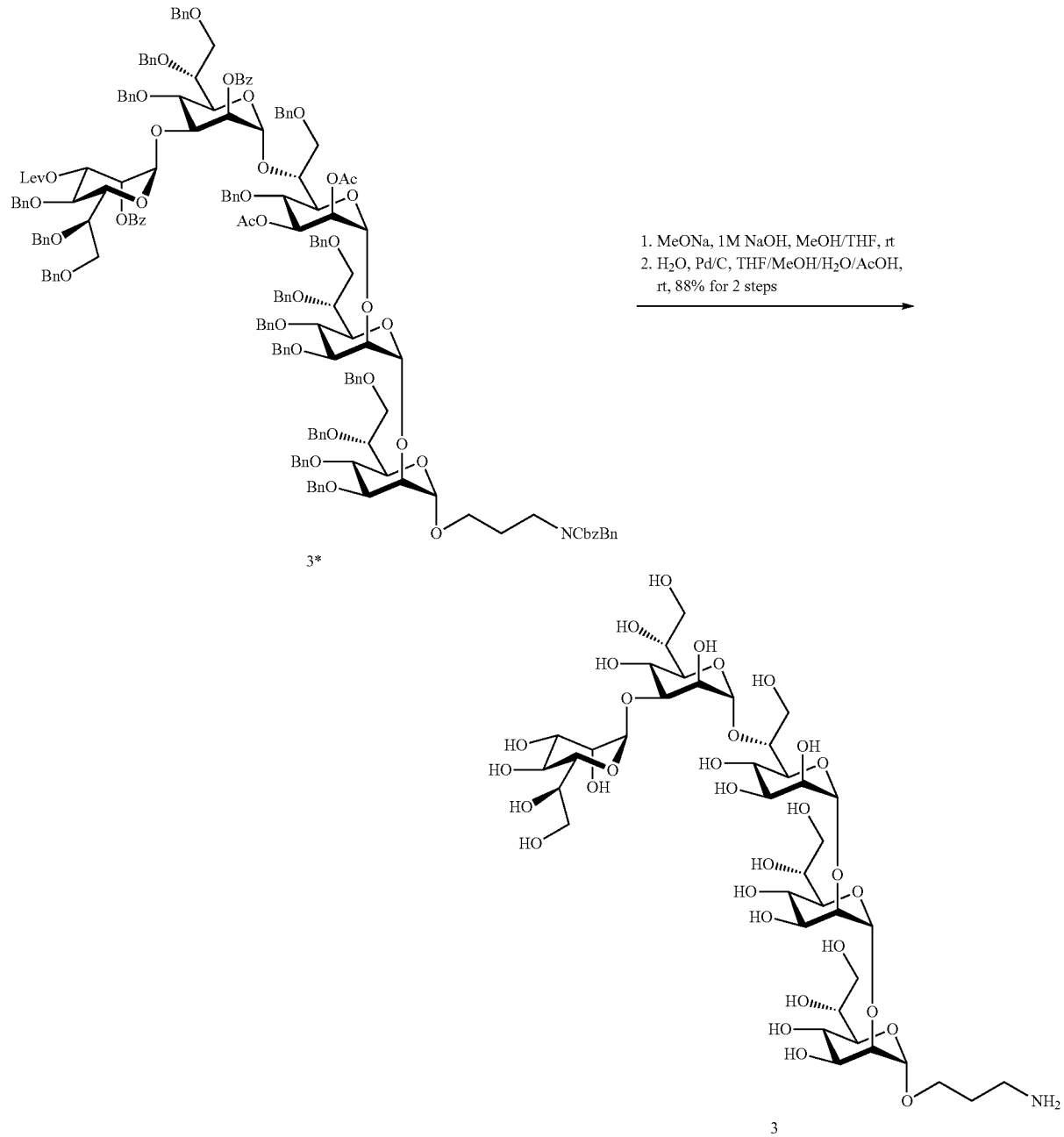

Compound 3* (25 mg, 0.0081 mmol) was dissolved in THF/MeOH (1:1, v/v, 2.0 mL), CH$_3$ONa (20 mg) was added, and the mixture was stirred at room temperature for 0.5 hr, followed by the addition of NaOH (aq, 1 M, 200 μL). The reaction mixture was stirred at room temperature for 12 hr. After the completion of the reaction was detected by TLC, Amerlite IR 120 (H$^+$) resin was added to neutralize the pH of the reaction solution to less than 7, the solution was filtered, and the filtrate was concentrated under reduced pressure, and was separated and purified by silica gel column chromatography (dichloromethane/methanol: 50/1) to obtain a half-deprotected product intermediate. The above deacylated compound was dissolved in MeOH/THF/H$_2$O/AcOH (10:5:4:1, v/v/v/v, 2 mL), 10% Pd/C (50 mg) was added, and the reaction mixture was stirred under hydrogen (1 bar) conditions for 48 hr. After the completion of the reaction was detected by time-of-flight mass spectrometry, the solution was filtered, the filtrate was concentrated and vacuum-dried, and the crude product was separated and purified by a Sephadex LH-20 gel column to obtain compound 3 (7.4 mg, 88% for two steps). $^1$H NMR (700 MHz, Deuterium Oxide) δ 5.14-5.11 (m, 1H, 1-H), 5.09-5.08 (m, 1H, 1-H), 5.07-5.06 (m, 1H, 1-H), 5.04-5.00 (m, 1H, 1-H), 4.95-4.93 (m, 1H, 1-H), 4.12 (t, J=2.4 Hz, 1H), 4.03-3.95 (m, 12H), 3.92 (dd, J=9.3, 3.3 Hz, 1H), 3.90-3.87 (m, 2H), 3.84 (d, J=9.7 Hz, 1H), 3.83-3.79 (m, 3H), 3.79-3.68 (m, 12H), 3.68-3.60 (m, 5H), 3.59 (dd, J=10.0, 2.8 Hz, 1H), 3.57-3.49 (m, 3H), 3.05 (tq, J=12.9, 7.4, 6.6 Hz, 2H, $CH_2$), 1.98-1.86 (m, 2H, $CH_2$). $^{13}$C NMR (176 MHz, Deuterium Oxide) δ 102.1, 102.0, 100.5, 99.1, 98.1, 78.7, 78.4, 78.2, 77.4, 74.0, 73.6, 73.3, 73.1, 72.3, 72.1, 71.6, 71.4, 70.7, 70.6, 70.4, 70.1, 69.9, 69.6, 69.6, 67.5, 67.5, 67.4, 66.8, 66.5, 64.9, 62.0, 62.0, 61.7, 61.6, 61.5, 37.5, 26.7. HRMS (ESI) m/z calcd for $C_{38}H_{70}O_{31}N$ $[M+H]^+$ 1036.3926, found 1036.3958.

Compound 4:

filtered, and the filtrate was concentrated under reduced pressure, and was separated and purified by silica gel column chromatography (dichloromethane/methanol: 50/1) to obtain a half-deprotected product intermediate. The above deacylated compound was dissolved in $MeOH/THF/H_2O/AcOH$ (10:5:4:1, v/v/v/v, 2 mL), 10% Pd/C (40 mg) was added, and the reaction mixture was stirred under hydrogen (1 bar) conditions for 48 hr. After the completion of the reaction was detected by time-of-flight mass spectrometry, the solution was filtered, the filtrate was concentrated and vacuum-dried, and the crude product was separated and purified by a Sephadex LH-20 gel column to obtain compound 4 (5.9 mg, 85% for two steps). $^1$H NMR (700 MHz, Deuterium Oxide) δ 5.05 (s, 1H, 1-H), 5.03 (s, 2H, 1-H), 5.02 (s, 1H, 1-H), 4.77 (s, 1H, 1-H), 4.17 (d, J=3.6 Hz, 2H), 4.04 (s, 1H), 3.99 (qd, J=7.1, 3.5 Hz, 5H), 3.93-3.87 (m, 3H),

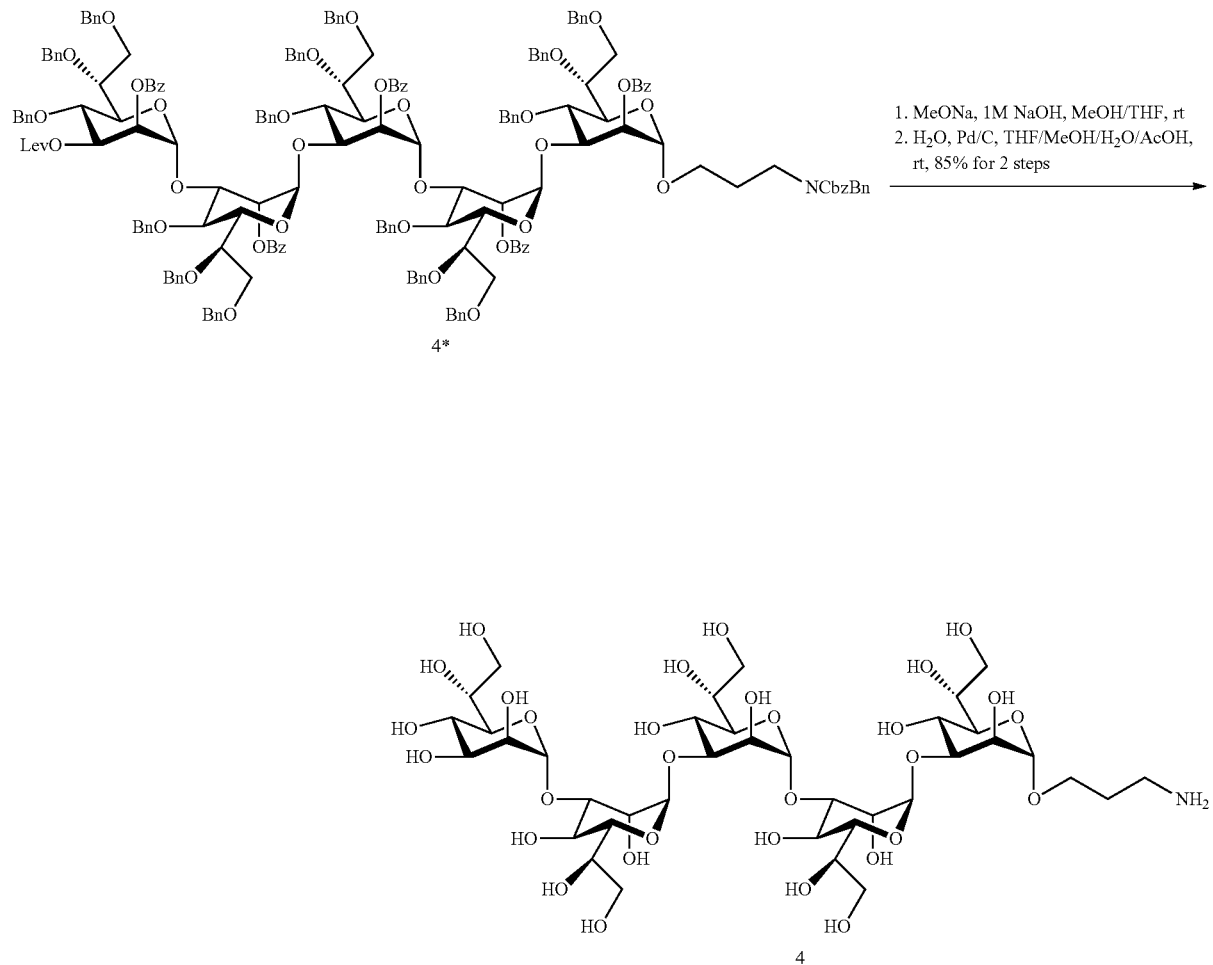

Compound 4* (20 mg, 0.0062 mmol) was dissolved in THF/MeOH (1:1, v/v, 2.0 mL), $CH_3ONa$ (15 mg) was added, and the mixture was stirred at room temperature for 0.5 hr, followed by the addition of NaOH (aq, 1 M, 100 μL). The reaction mixture was stirred at room temperature for 12 hr. After the completion of the reaction was detected by TLC, Amerlite IR 120 ($H^+$) resin was added to neutralize the pH of the reaction solution to less than 7, the solution was 3.86-3.71 (m, 13H), 3.71-3.61 (m, 7H), 3.59-3.50 (m, 2H), 3.14-2.98 (m, 2H, $CH_2$), 1.92 (q, J=7.6 Hz, 2H, $CH_2$). $^{13}$C NMR (176 MHz, Deuterium Oxide) δ 102.2, 102.1, 102.1, 102.0, 99.6, 78.1, 77.9, 77.9, 77.8, 73.9 (d, J=2.0 Hz), 73.8, 73.8, 73.1, 71.5, 71.4, 71.3, 70.6, 69.9, 69.4, 69.4, 67.4, 66.8, 66.7, 66.7, 64.9, 61.6, 61.5, 37.5, 26.6. HRMS (ESI) m/z calcd for $C_{38}H_{70}O_{31}N$ $[M+H]^+$ 1036.3926, found 1036.3911.

Compound 5:

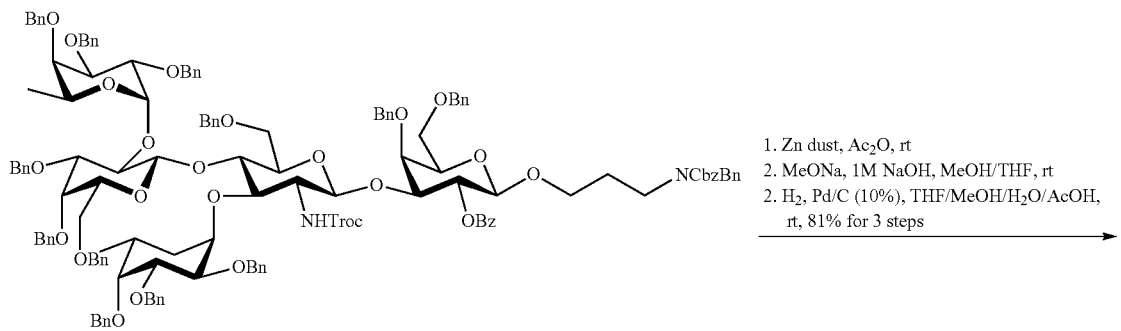

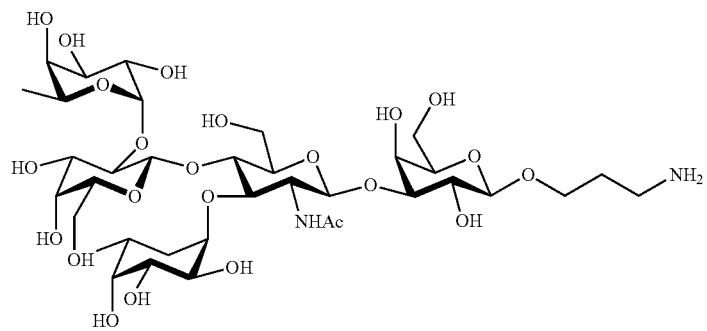

Compound 5* (12 mg, 0.0049 mmol) was dissolved in Ac₂O (1 mL), newly activated zinc powder (50 mg) was added, and the reaction mixture was stirred at room temperature for 15 hr. After the disappearance of the raw materials was detected by TLC, the solution was filtered, and the filtrate was concentrated under reduced pressure and vacuum-dried to obtain an NAc product intermediate. The above product intermediate was dissolved in THF/MeOH (1:1, v/v, 1 mL), CH₃ONa (10 mg) was added, and the mixture was stirred at room temperature for 0.5 hr, followed by the addition of NaOH (aq, 1 M, 100 μL). The reaction mixture was stirred at room temperature for 12 hr. After the completion of the reaction was detected by TLC, Amerlite IR 120 (H⁺) resin was added to neutralize the pH of the reaction solution to less than 7, the solution was filtered, and the filtrate was concentrated under reduced pressure, and was separated and purified by silica gel column chromatography (dichloromethane/methanol: 50/1) to obtain the product intermediate. The above deacylated compound was dissolved in MeOH/THF/H₂O/AcOH (10:5:4:1, 1 mL), 10% Pd/C (40 mg) was added, and the reaction mixture was stirred under hydrogen (1 bar) conditions for 48 h. After the completion of the reaction was detected by time-of-flight mass spectrometry, the solution was filtered, the filtrate was concentrated and vacuum-dried, and the crude product was separated and purified by a Sephadex LH-20 gel column to obtain compound 5 (3.6 mg, 81% for three steps). $^1$H NMR (700 MHz, Deuterium Oxide) δ 5.20 (d, J=3.5 Hz, 1H, 1-H), 5.04 (d, J=4.0 Hz, 1H, 1-H), 4.80 (q, J=6.8 Hz, 1H), 4.65 (d, J=8.4 Hz, 1H, CH₂), 4.44 (d, J=7.8 Hz, 1H, CH₂), 4.33 (d, J=8.0 Hz, 1H, CH₂), 4.18 (q, J=6.7 Hz, 1H), 4.09-4.04 (m, 1H), 3.97 (dt, J=11.3, 6.4 Hz, 1H), 3.93 (d, J=11.9 Hz, 1H), 3.91-3.83 (m, 3H), 3.79 (dq, J=12.5, 6.0, 4.6 Hz, 3H), 3.76-3.68 (m, 6H), 3.67-3.58 (m, 5H), 3.58-3.51 (m, 4H), 3.49 (t, J=8.8 Hz, 1H), 3.38 (d, J=9.6 Hz, 1H), 3.08 (h, J=6.2 Hz, 2H, CH₂), 1.95 (s, 3H, CH₃CO), 1.92 (dt, J=13.2, 6.6 Hz, 2H, CH₂), 1.19 (d, J=6.6 Hz, 3H, Fucose-CH₃), 1.16 (d, J=6.6 Hz, 3H, Fucose-CH₃). $^{13}$C NMR (176 MHz, Deuterium Oxide) δ 174.7, 102.9, 102.4, 100.2, 99.4, 98.6, 82.3, 76.4, 75.4, 74.8, 74.7, 74.7, 73.5, 73.0, 71.9, 71.7, 69.7, 69.7, 69.1, 68.7, 68.3, 68.2, 67.9, 67.7, 66.9, 66.8, 61.5, 61.4, 60.9, 59.8, 37.6, 26.8, 22.3, 15.4 (d, J=2.4 Hz). HRMS (ESI) m/z calcd for $C_{35}H_{63}O_{24}N_2$ [M+H]⁺ 895.3765, found 895.3766.

Compound 6:

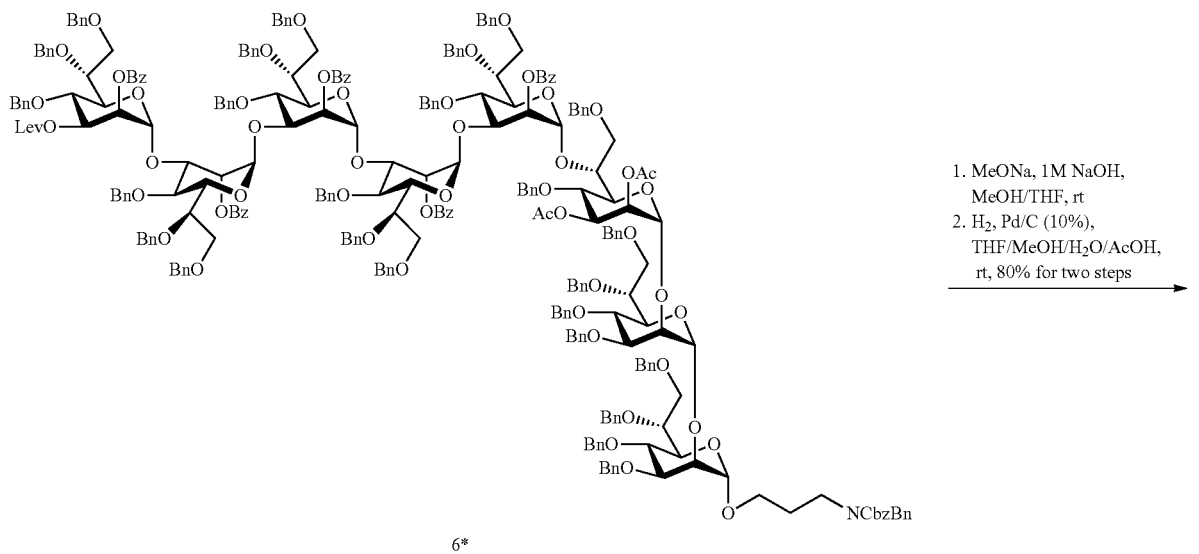

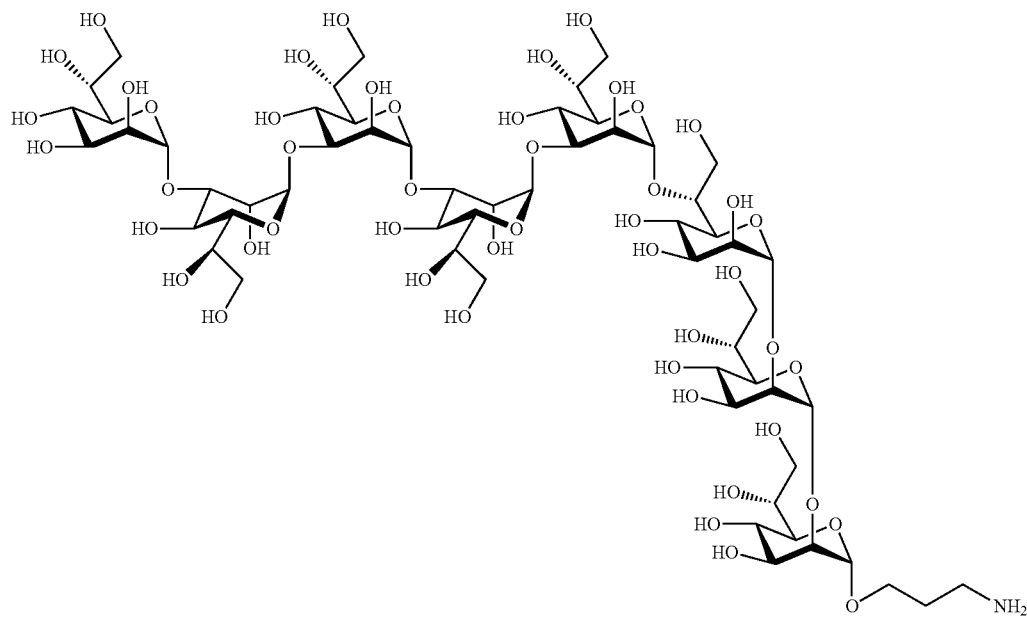

Compound 6* (20 mg, 4.2 μmol) was dissolved in THF/MeOH (1:1, 2 mL), MeONa (50 mg) was added, and the mixture was stirred at room temperature for 0.5 hr, followed by the addition of NaOH (aq, 1 M, 100 μL). The reaction mixture was stirred at room temperature for 12 hr. After the completion of the reaction was detected by TLC, Amerlite IR 120 (H+) resin was added to neutralize the pH of the reaction solution to less than 7, the solution was filtered, and the filtrate was concentrated under reduced pressure, and was separated and purified by silica gel column chromatography (dichloromethane/methanol:50/1) to obtain the product intermediate. The above deacylated compound was dissolved in MeOH/THF/H$_2$O/AcOH (10:5:4:1, v/v/v/v, 2 mL), 10% Pd/C (40 mg) was added, and the reaction mixture was stirred under hydrogen (1 bar) conditions for 48 hr. After the completion of the reaction was detected by time-of-flight mass spectrometry, the solution was filtered, the filtrate was concentrated and vacuum-dried, and the crude product was separated and purified by a Sephadex LH20 gel column to obtain compound 6 (5.4 mg, 80% for two steps). $^1$H NMR (700 MHz, Deuterium Oxide) δ 5.13 (s, 1H, 1-H), 5.09 (s, 1H, 1-H), 5.04 (d, J=2.0 Hz, 2H, 1-H), 5.03 (s, 3H, 1-H), 5.02 (s, 1H, 1-H), 4.94 (d, J=1.8 Hz, 1H, 1-H), 4.17 (p, J=1.9 Hz, 4H), 4.12 (t, J=2.5 Hz, 1H), 3.98 (dt, J=10.2, 3.5 Hz, 16H), 3.90 (ddd, J=13.9, 8.9, 2.9 Hz, 8H), 3.85-3.72 (m, 23H), 3.72-3.68 (m, 3H), 3.68-3.61 (m, 8H), 3.60 (dd, J=9.6, 6.7 Hz, 1H), 3.58-3.56 (m, 1H), 3.56-3.50 (m, 3H), 3.03 (ddt, J=14.7, 12.7, 6.5 Hz, 2H, CH$_2$), 1.96-1.86 (m, 2H, CH$_2$). $^{13}$C NMR (176 MHz, Deuterium Oxide) δ 102.2, 102.1, 100.5, 98.1, 78.6, 78.2, 78.0, 77.8, 77.7, 73.9, 73.8, 73.7, 73.3, 73.2, 72.4, 72.1, 71.6, 71.4, 71.3, 70.7, 70.6, 70.4, 70.2, 69.9, 69.6, 69.5, 68.1, 67.5, 67.4, 66.8, 66.7, 65.0, 62.0, 61.7, 61.6, 61.5, 61.4, 37.5, 26.9, 25.3. HRMS (ESI) m/z calcd for C$_{59}$H$_{106}$O$_{49}$N [M+H]$^+$ 1612.5828, found 1612.5831.

Compound 7:

Compound 7* (9 mg, 0.0014 mmol) was dissolved in AcOH (1 mL), newly activated zinc powder (50 mg) was added, and the reaction mixture was stirred at room temperature for 12 hr. After the disappearance of the raw materials was detected by TLC, the solution was filtered, and the filtrate was concentrated under reduced pressure. Then, a proper amount of DCM was added for dilution, and the solution was washed with saturated NaHCO$_3$ and dried with anhydrous Na$_2$SO$_4$. After the solution was filtered, the filtrate was concentrated under reduced pressure and vacuum-dried to obtain an NAc product intermediate. The above product intermediate was dissolved in THF/MeOH (1:1, 1 mL), MeONa (10 mg) was added, and the mixture was stirred at room temperature for 15 min, followed by the addition of NaOH (aq, 1 M, 100 μL). The reaction mixture was stirred at room temperature for 12 h. After the completion of the reaction was detected by TLC, Amerlite IR 120 (H$^+$) resin was added to neutralize the pH of the reaction solution to 7, the solution was filtered, and the filtrate was concentrated under reduced pressure, and was separated and purified by silica gel column chromatography (dichloromethane/methanol: 50/1) to obtain the product intermediate. The above deacylated compound was dissolved in MeOH/THF/H$_2$O/AcOH (10:5:4:1, 1 mL), 10% Pd/C (40 mg) was added, and the reaction mixture was stirred under hydrogen (1 bar) conditions for 24 hr. After the completion of the reaction was detected by time-of-flight mass spectrometry, the solution was filtered, the filtrate was concentrated and vacuum-dried, and the crude product was separated and purified by a Sephadex LH20 gel column to obtain compound 7 (3 mg, 82% for three steps). $^1$H NMR (700 MHz, D$_2$O) δ=5.20 (d, J=2.8 Hz, 1H, anomeric H), 5.13 (s, 1H, anomeric H), 5.10 (s, 1H, anomeric H), 5.09 (s, 1H, anomeric H), 5.06-5.01 (m, 5H, anomeric H), 4.95 (s, 1H, anomeric H), 4.82-4.78 (m, 1H), 4.65 (d, J=8.6 Hz, 1H, anomeric H), 4.44 (dd, J=7.8, 4.1 Hz, 2H), 4.21-4.14 (m, 6H), 4.12 (s, 1H), 4.06 (s, 1H), 3.99 (t, J=9.7 Hz, 10H), 3.95-3.86 (m, 8H), 3.86-3.68 (m, 37H), 3.64 (dt, J=21.4, 9.9 Hz, 14H), 3.60-3.50 (m, 5H), 3.41-3.36 (m, 1H), 3.11-3.01 (m, 2H, CH$_2$), 1.95 (s, 3H, CH$_3$CO), 1.94-1.89 (m, 2H, CH$_2$), 1.19 (d, J=6.5 Hz, 3H, Fucose-CH$_3$), 1.16 (d, J=6.5 Hz, 3H, Fucose-CH$_3$). $^{13}$C NMR (176 MHz, D$_2$O) δ=158.8, 102.6 (anomeric), 102.1 (anomeric), 102.04 (anomeric), 101.99 (anomeric), 101.9 (anomeric), 101.7 (anomeric), 101.2 (anomeric), 100.5 (anomeric), 100.2 (anomeric), 99.4 (anomeric), 99.2 (anomeric), 98.5 (anomeric), 98.1 (anomeric), 82.1, 79.7, 79.0, 78.6, 78.6, 78.2, 77.9, 77.8, 76.3, 75.4, 74.8, 74.8, 74.0, 73.9, 73.8, 73.7, 73.5, 73.2, 73.1, 72.1, 71.9, 71.7, 71.5, 71.39, 71.36, 71.3, 70.6, 70.4, 70.1, 69.9, 69.7, 69.5, 69.45, 69.44, 69.41, 69.1, 68.7, 68.4, 68.3, 67.75, 67.68, 67.5, 67.46, 66.9, 66.81, 66.77, 66.7, 66.68, 66.67, 66.0, 65.9, 65.7, 64.9, 62.05, 62.0, 61.73, 61.69, 61.6, 61.5, 61.47, 61.46, 61.0, 59.8, 37.5, 26.6, 22.3, 15.4. HR-ESI-MS (m/z): calcd for C$_{91}$H$_{160}$O$_{72}$N$_2$ [M+2H]$^{2+}$ 1216.4455, found 1216.4287; C$_{91}$H$_{160}$O$_{72}$N$_2$K [M+2H+K]$^{3+}$ 823.9514, found 823.9442.

Example 2. Culture and Inactivation of *Helicobacter pylori* Serotype O6 and Extraction of Lipopolysaccharide To culture the *Helicobacter pylori* serotype O6, the *Helicobacter pylori* serotype O6 was firstly cultured on blood agar plates at 37° C. in a gas atmosphere of 7% CO$_2$ for 72 hours, transferred into a *Brucella* Broth medium (ELITE-MEDIA), and cultured at 37° C. in a gas atmosphere of 7% CO$_2$ for 72 hours to obtain a bacterial solution.

To inactivate the *Helicobacter pylori* serotype O6, 5 mL of 4% paraformaldehyde was added to 50 mL of 1.7×10$^{11}$ CFU/mL bacterial solution until the final concentration was 0.4%, and the mixture was incubated at 37° C. for 72 hours. The cells were collected by centrifugation, washed twice with PBS (pH 7.4), finally diluted with PBS (pH 7.4) to 5×10$^{12}$ CFU/mL, and stored at 4° C.

Extraction of *Helicobacter pylori* serotype O6 lipopolysaccharide by a phenol-water method: The cells were collected by centrifugation and washed twice with a phosphate buffer solution (PBS, pH 7.4), and the wet weight of the precipitate was measured. The cells were resuspended with sterile water that was 3 times the mass of the wet weight of the cells to obtain a bacterial suspension, and the bacterial suspension was repeatedly frozen and thawed for 5 times. The bacterial suspension was mixed with an equal volume of 90% phenol. After being shaken in a thermostatic water bath, the mixed solution was cooled to 4° C. and centrifuged, and the upper aqueous phase was taken, followed by the addition of an equal volume of sterile water. After being shaken in a thermostatic water bath, the mixture was cooled to 4° C. and centrifuged, and the supernatant was taken. The two supernatants were combined and dialyzed with distilled water until no purple was detected by ferric chloride, and the solution was freeze-dried and stored.

Figure 2:
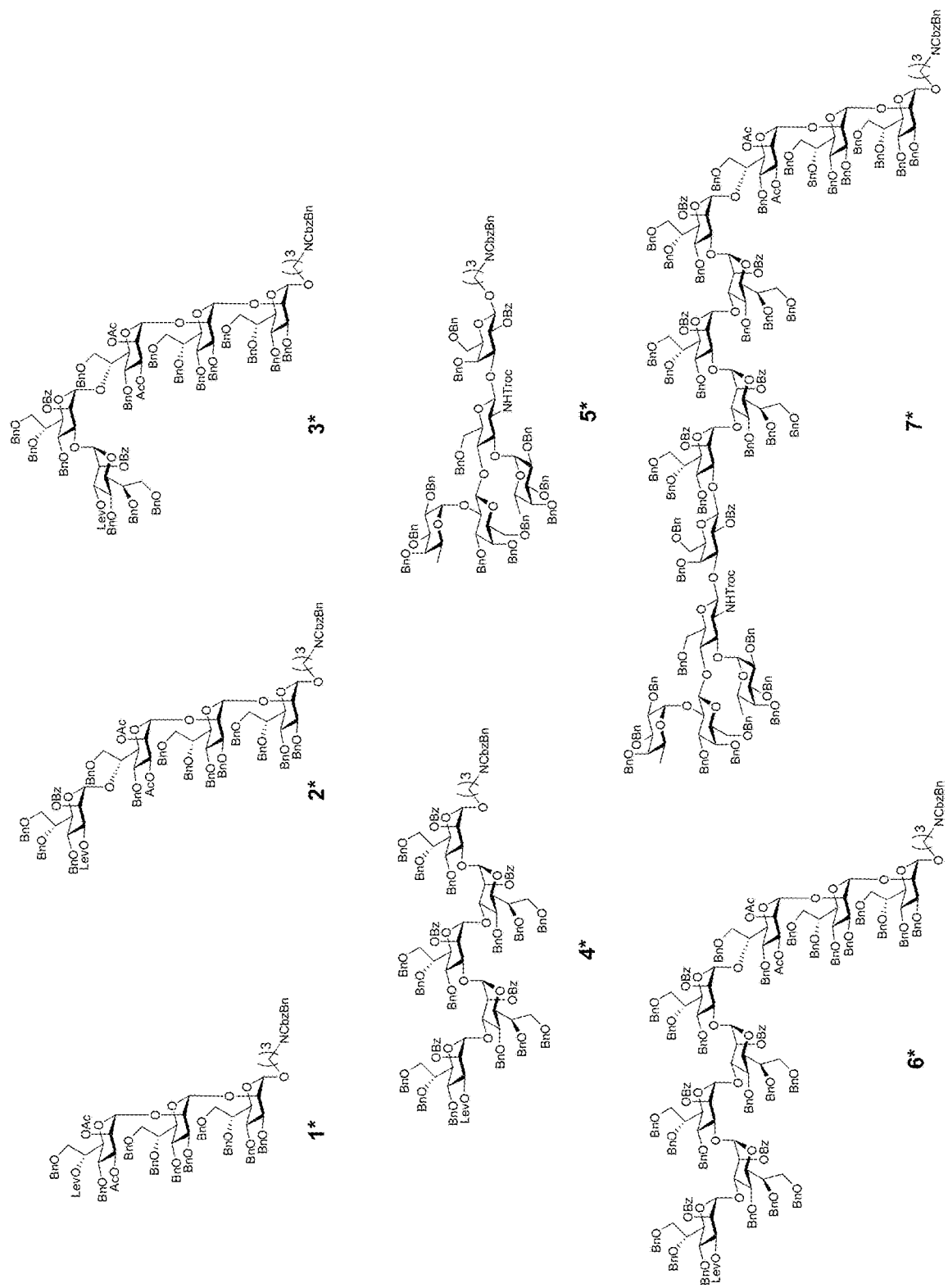
FIG. 2: Structural formulae of fully protected antigen oligosaccharide precursors 1*, 2*, 3*, 4*, 5*, 6* and 7*.
Figure 3:
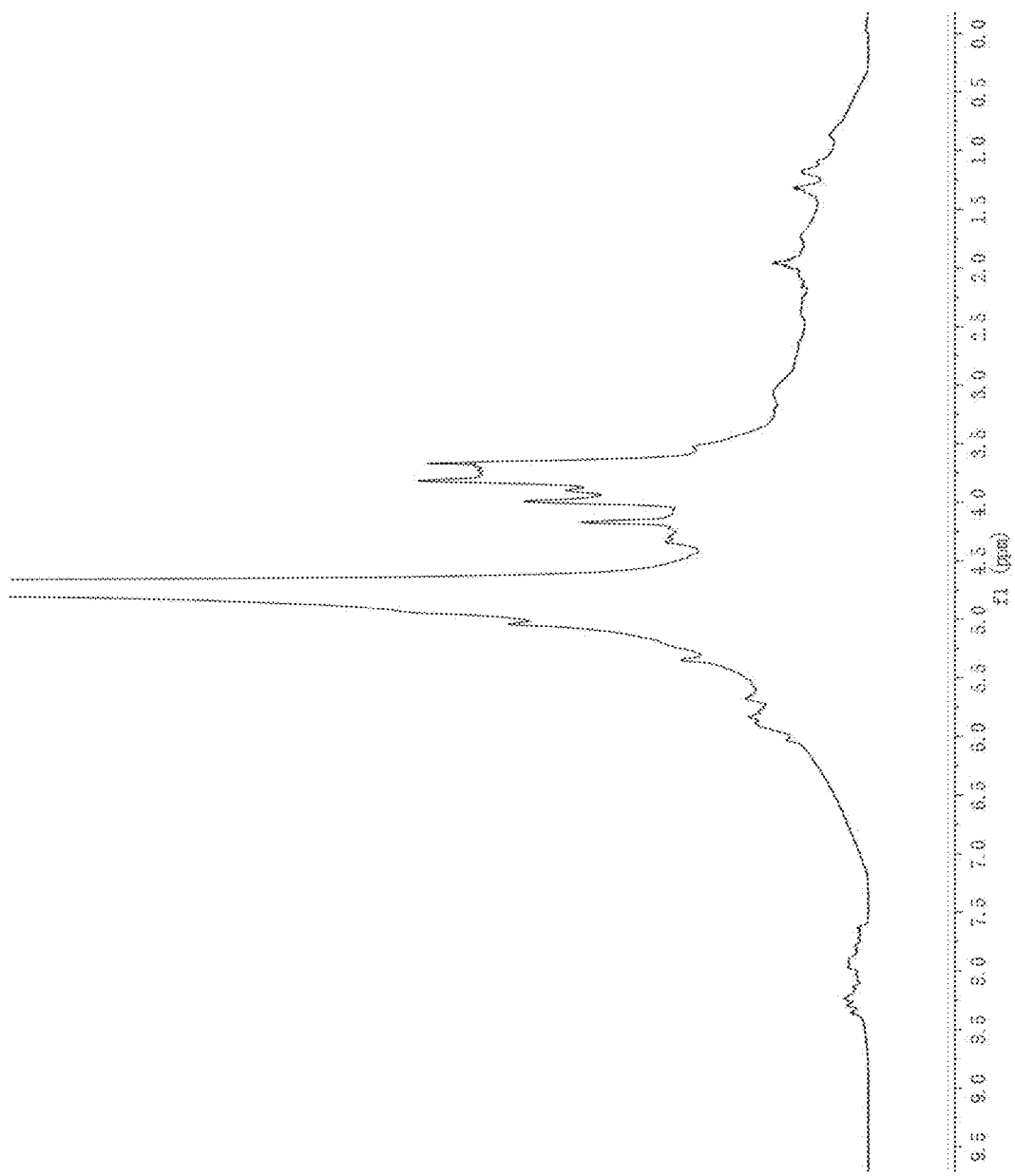
FIG. 3: $H^1$ NMR spectrogram of extracted *Helicobacter pylori* serotype O6 lipopolysaccharide.
Figure 4:
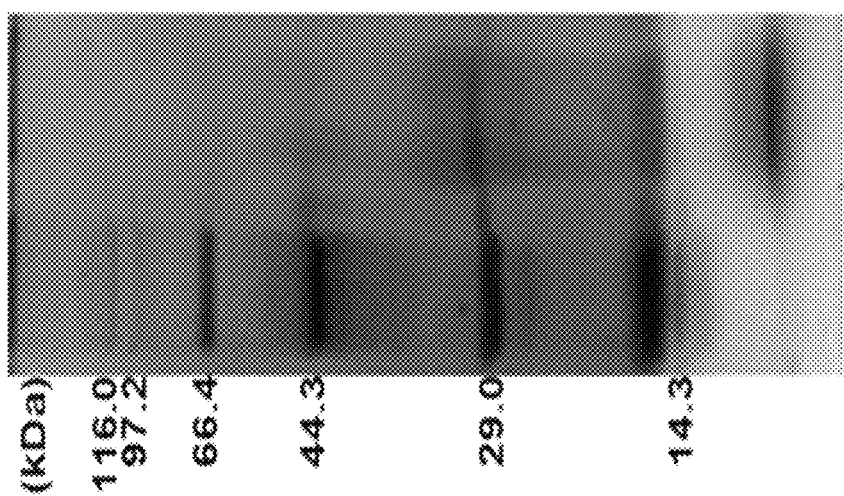
FIG. 4: Silver staining image of extracted *Helicobacter pylori* serotype O6 lipopolysaccharide.

The freeze-dried LPS powder was dissolved in Tris-HCl (100 mmol, pH 8.0), and 100 μg/ml DNase I and 50 μg/ml RNase A were added. After digestion at 37° C. overnight, 100 μg/ml proteinase K was added. After 2 hours of reaction, the mixture was boiled in boiling water at 100° C. for 10 min to inactivate the enzyme, the solution was cooled to 4° C. and centrifuged, and the supernatant was collected. Water-saturated phenol was added to the supernatant and uniformly mixed, the mixture was centrifuged again, and the supernatant was dialyzed and freeze-dried. Anhydrous ethanol was added to the freeze-dried powder until the final concentration was 85%. The mixture was precipitated at −20° C. overnight and centrifuged, the supernatant was discarded, and the precipitate was freeze-dried and weighed. The obtained freeze-dried powder had characteristic peaks of polysaccharides on the carbon chain when detected by H$^1$ NMR (FIG. 2). At chemical shift 1.95, there was a characteristic peak of N-acetylglucosamine (GlcNAc), and at chemical shift 1.18, there was a characteristic peak of fucose (Fucose-CH$_3$). SDS-PAGE electrophoresis and silver staining (FIGS. 3 and 4) showed that the extracted lipopolysaccharide had good purity, and the average molecular weight of the obtained lipopolysaccharide was mostly below 29 KDa.

Immunization Experiment of *Helicobacter pylori* Serotype O:6 Lipopolysaccharide:

1.8-2.2 kg New Zealand rabbits were divided into two groups, 3 as the experimental group and 3 as the control group. On day 0, the New Zealand rabbits in the experimental group were subcutaneously injected for immunization with 500 μL of a lipopolysaccharide-Freund's complete adjuvant 1:1 mixed emulsion at multiple points; and the New Zealand rabbits in the control group were injected with 500 μL of a PBS-Freund's complete adjuvant 1:1 mixed emulsion. On day 14 and day 28, Freund's incomplete adjuvant was used instead of Freund's complete adjuvant for booster immunization. The amount of antigen injected into each of the New Zealand rabbits in the experimental group each time was equivalent to 400 μg of lipopolysaccharide antigen. The New Zealand rabbit serum on day 35 was taken for ELISA assay.

Figure 5:
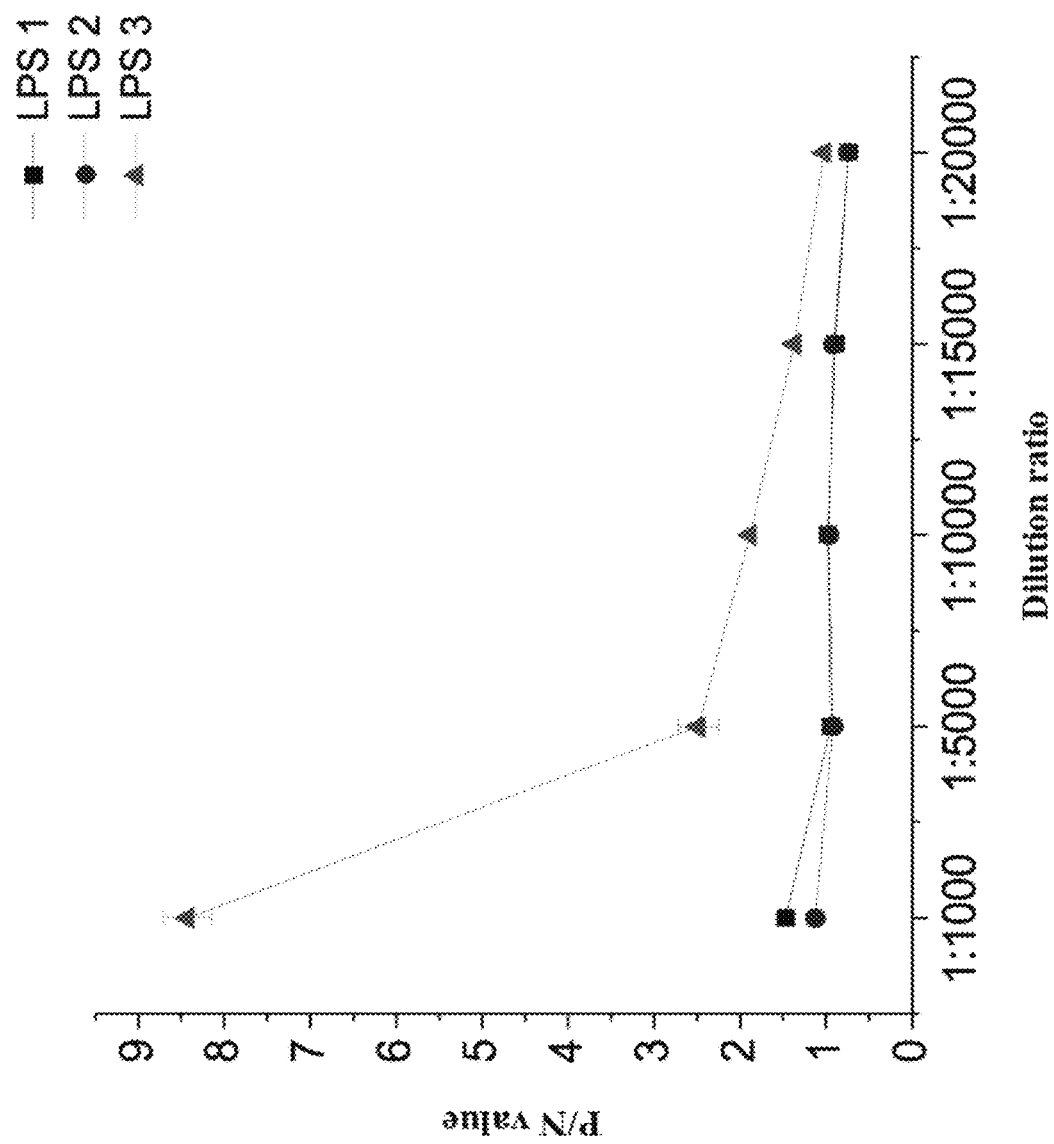
FIG. 5: ELISA assay of antibody effective titer in rabbit serum.

ELISA Assay of *Helicobacter pylori* Serotype O:6 Lipopolysaccharide Antiserum:

After the LPS was diluted with 0.05 M CBS buffer (pH 9.6) to 20 μg/mL, an ELISA well plate was coated with the solution, 100 μL/well. After 24 h of coating at 4° C., the well plate was washed with PBST (PBS containing 0.1% tween-20) three times and patted dry. A blocking buffer (PBST containing 5% skimmed milk) was added to the coated ELISA well plate according to 300 μL/well, the plate was sealed with a sealer for blocking at 25° C. for 6 hr. The blocking buffer was discarded, and the well plate was washed with PBST three times and patted dry. Different gradients of rabbit serum diluted with 1% BSA-PBS (w/v) were added to the coated well plate, 100 μL/well. Incubation was carried out at 37° C. for 2 hr, and the well plate was washed with PBST four times and patted dry. A horseradish peroxidase-labeled goat anti-rabbit secondary antibody diluted 1:50000 was respectively added, 100 μL/well, and incubated at 37° C. for 1 hr. The well plate was washed with PBST four times and patted dry. A 200 μL/well TMB color developing solution was used for incubation at 37° C. in the dark, and the incubation was terminated with 50 μL/well 2 M $H_2SO_4$ immediately after the color development. The absorbance at 450 nm was measured. The antibody titer as shown in FIG. 5 was obtained. The rabbit serum with the highest antibody titer was selected for glycochip screening. In the ELISA assay, we found that the serum of the New Zealand rabbits injected with the *Helicobacter pylori* serotype O6 LPS could bind to the extracted LPS, and the antibody effective titer in the serum reached 1:10000.

Example 3. Application of Oligosaccharide Compounds in Preparation of Vaccine Against *Helicobacter pylori*

Preparation of Glycoprotein Conjugate of Oligosaccharide Compound and CRM-197

Triethylamine (12 μL, 86 μmol) was added to bis(p-nitrophenyl adipate) (PNP, 26.33 mg, 67.8 μmol) in DMSO/pyridine (1:1, 25 mL: 0.25 mL), and the mixture was stirred at room temperature for 5 minutes. The oligosaccharide compound (1.6 mg, 2.26 μmol) dissolved in DMSO/pyridine (1/1, 0.1 mL: 0.1 mL) was added dropwise, and the mixture was stirred at room temperature to react for 7 hours. TLC detection showed that the raw materials had reacted completely, and sugar stain (0.1% (v/v) 3-methoxyphenol, 2.5% (v/v) sulfuric acid-ethanol) showed the presence of the product. The reaction mixture was freeze-dried. The freeze-dried solid was washed with chloroform (1 mL) 6 times to obtain oligosaccharide-PNP ester. $CRM_{197}$ protein (1 mg, 0.017 μmol) was washed with sterile water (400 μL) 3 times in an ultrafiltration tube, and then washed once with a phosphate solution (pH 8.0, 400 μL). The washed $CRM_{197}$ protein was added to the ligosaccharide-PNP ester and stirred at room temperature for 24 hours. The reaction mixture was washed with sterile water and a phosphate solution to obtain the glycoprotein conjugate. MALDI-TOF/TOF-MS and SDS-PAGE were used to identify the obtained glycoprotein conjugate.

Glycoconjugate immunization experiment: 8 six-week-old Balb/c mice were divided into two groups, 5 as the experimental group and 3 as the control group. On day 0, the mice in the experimental group were subcutaneously injected for immunization with 100 μL of a glycoconjugate-Freund's complete adjuvant 1:1 mixed emulsion; and the mice in the control group were injected with 100 μL of a PBS-Freund's complete adjuvant 1:1 mixed emulsion. On day 14 and day 28, a Freund's incomplete adjuvant was used instead of a Freund's complete adjuvant for booster immunization. The amount of the antigen injected into each of the mice in the experimental group each time was equivalent to 4 μg of carbohydrate antigen. The sera on day 0, day 7, day 14, day 21 and day 35 were taken for chip detection.

Construction and Testing of Oligosaccharide Chip

A chemically synthesized oligosaccharide antigen was fixed onto the chip surface through an amino linker, and the antiserum was incubated with the oligosaccharide chip and then incubated with the secondary antibody.

Under a chip scanner, the fluorescence of the binding of the oligosaccharide fragment and the antibody can be obtained. In this way, the binding strength of the oligosaccharide fragment to the antibody in the serum can be quantified, the amount of the chemically synthesized oligosaccharide and antiserum can be saved, and the result can be reflected clearly.

Application of the oligosaccharide chip in the detection process of the antibody in the antiserum in immunogenicity research:

The experimental procedure is as follows:
(1) Activated amino slides were spotted with a biochip spotter. After the completion of the spotting, incubation was carried out overnight at a temperature of 26° C. and a humidity of 55%.
(2) Then the slides were immersed in a solution B (50 nM $Na_2HPO_4$, 100 nM ethanolamine in water) at 50° C. for 1 hour. The slides were washed with ultrapure water 3 times, and the residual water was removed by centrifugation.
(3) 3% BSA (w/v) in PBS was used for blocking at 4° C. overnight. The slides were washed with PBST (PBS containing 0.1% tween) once, washed with PBS twice, and centrifugally dried.
(4) The slides were placed into a 16-well incubator (ProPlate). 120 μL of mouse serum sample diluted 1:50 in 1% BSA (w/v) in PBS was added to each well, and incubated in a 37° C. wet box in the dark for 1 hour. The sample was removed, and the incubator was washed with 150 μL of PBST 3 times.
(5) A secondary antibody diluted 1:400 in 1% BSA (w/v) in PBS was added, and incubated in a wet box at 37° C. in the dark for 45 minutes. The secondary antibody solution was removed, and the incubator was washed with 150 μL of PBST 3 times. The 16-well incubator was removed, washed with ultrapure water, and washed with ultrapure water for 15 minutes. The residual water was removed by centrifugation. Scanning was carried out using the chip scanner.

Figure 6A:
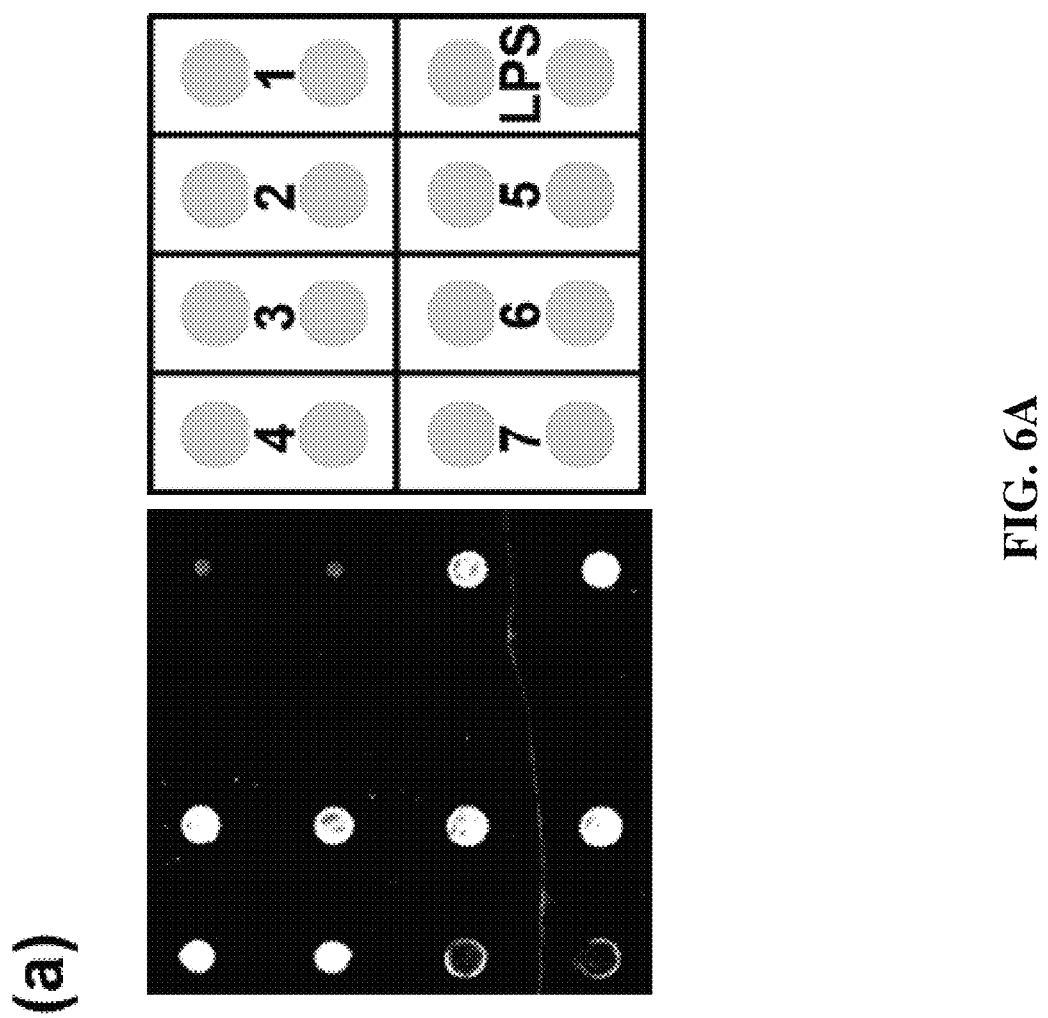
FIG. 6A: Detection of the antibody binding activity of the synthetic oligosaccharides in the oligosaccharide chip using an anti-rabbit IgG FITC-labeled secondary antibody. The chip spotting mode is shown as follows:
1: trisaccharide 1, spotting concentration is 1 mM;
2: tetrasaccharide 2, spotting concentration is 1 mM;
3: heptoglycan-chain-containing pentasaccharide 3, spotting concentration is 1 mM;
4: heptoglycan-chain-containing pentasaccharide 4, spotting concentration is 1 mM;
5: pentasaccharide 4 containing only Lewis O-antigen, spotting concentration is 1 mM;
6: heptoglycan-chain-containing octasaccharide 6, spotting concentration is 1 mM;
7: tridecasaccharide 7 containing Lewis O-antigen, spotting concentration is 1 mM; and
8: *Helicobacter pylori* serotype O6 lipopolysaccharide, spotting concentration is 1 mg/mL.
Figure 6B:
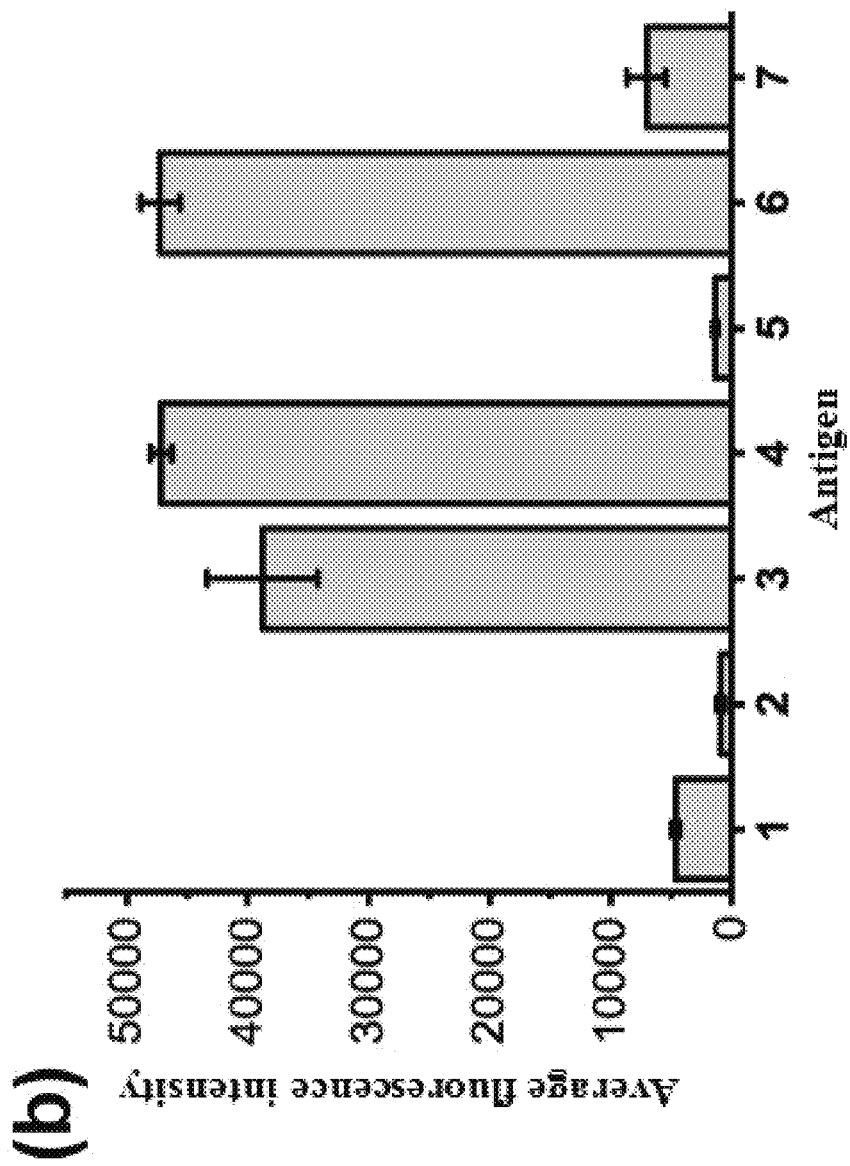
FIG. 6B: quantitative measurements of average fluorescence intensity of spots 1-7 in FIG. 6A. Error bars are standard deviations of 4 different points from two different detection areas.

Immunogenicity Detection of *Helicobacter pylori* Serotype O:6 Synthetic Oligosaccharide Fragment:

NHS slides (SurModics, DN01-0025) were spotted with synthetic oligosaccharide compounds 1 to 7 using a biochip spotter (Jiangsu RayMe Biotechnology Co., Ltd.). After the completion of the spotting, incubation was carried out overnight at a temperature of 26° C. and a humidity of 55%. Then the slides were immersed in a solution B (50 nM Na$_2$HPO$_4$, 100 nM ethanolamine in water) at 50° C. for 1 hour. The slides were washed with ultrapure water 3 times, and the residual water was removed by centrifugation. 3% BSA (w/v) in PBS was used for blocking at 4° C. overnight. The slides were washed with PBST (PBS containing 0.1% tween) once, washed with PBS twice, and centrifugally dried. The slides were placed into a 16-well incubator (ProPlate). 120 μL of mouse serum sample diluted 1:50 in 1% BSA (w/v) in PBS was added to each well, and incubated in a 37° C. wet box in the dark for 1 hour. The sample was removed, and the incubator was washed with 150 μL of PBST 3 times. A secondary antibody diluted 1:400 in 1% BSA (w/v) in PBS was added, and incubated in a wet box at 37° C. in the dark for 45 minutes. The secondary antibody solution was removed, and the incubator was washed with 150 μL of PBST 3 times. The 16-well incubator was removed, washed with ultrapure water, and washed with ultrapure water for 15 minutes. The residual water was removed by centrifugation. Scanning was carried out using the chip scanner. The results shown in FIG. 6A and FIG. 6B were obtained: pentasaccharide 3, pentasaccharide 4 and octasaccharide 6 have higher fluorescence intensity. It can be seen from the result that the serum antibodies generated against the *Helicobacter pylori* serotype O:6 purified polysaccharide have obvious and strong recognition and binding to fragments containing α-(1→3)-heptoglycan chain (pentasaccharide 3, pentasaccharide 4 and octasaccharide 6), but do not recognize Lewis structure 5 and tridecasaccharide 7 also containing an α-(1→3)-heptoglycan chain, indicating that the Lewis structure may hinder the immune recognition of heptoglycan by antibodies. Therefore, the α-(1→3)-heptoglycan chain is an important immune epitope and heptoglycan-containing saccharides can be used as an important antigenic material for saccharide vaccines against *Helicobacter pylori*.

What is claimed is:

1. A method for preparing a vaccine against *Helicobacter pylori*, comprising the step of incorporating a heptoglycan-chain-containing oligosaccharide of the structure (I) as an active component in the vaccine formulation (I)

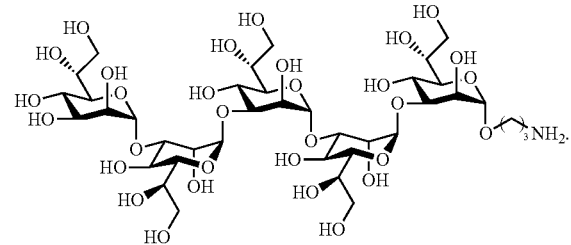

2. The method of claim 1, wherein a synthesis process of the heptoglycan-chain-containing oligosaccharide is as follows:

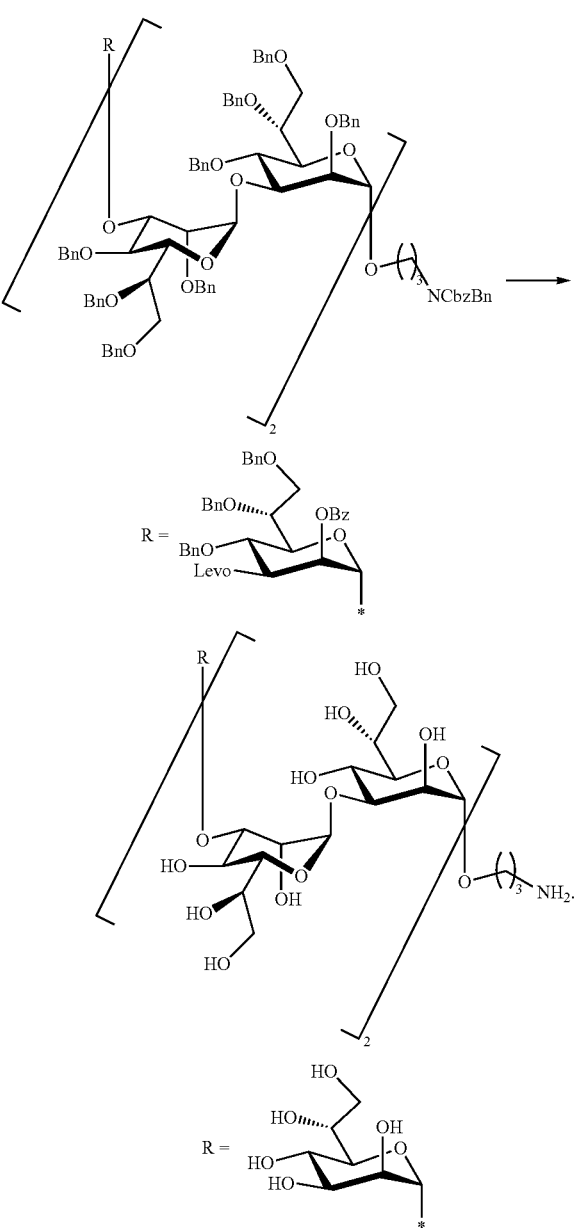

3. An oligosaccharide chip, wherein the oligosaccharide chip is prepared by fixing the heptoglycan-chain-containing oligosaccharide of claim 1 onto a chip surface through an amino linker of the oligosaccharide.

4. A vaccine for the prevention and treatment of *Helicobacter pylori* infection, comprising the heptoglycan-chain-containing oligosaccharide of claim 1 as an active component.

* * * * *